(12) United States Patent
Manning et al.

(10) Patent No.: US 10,493,149 B2
(45) Date of Patent: *Dec. 3, 2019

(54) STABLE ANTI-OSMR ANTIBODY FORMULATION

(71) Applicant: Kiniksa Pharmaceuticals, Ltd., Hamilton (BM)

(72) Inventors: Mark Cornell Manning, Johnstown, CO (US); Zahra Shahrokh, Weston, MA (US); Dave Nichols, Wellesley, MA (US); Phillip M Levesque, Wellesley, MA (US); Ryan Erik Holcomb, Johnstown, CO (US)

(73) Assignee: Kiniksa Pharmaceuticals, Ltd., Hamilton (BM)

(*) Notice: Subject to any disclaimer, the term of this patent is extended or adjusted under 35 U.S.C. 154(b) by 0 days.

This patent is subject to a terminal disclaimer.

(21) Appl. No.: 15/950,974

(22) Filed: Apr. 11, 2018

(65) Prior Publication Data

US 2018/0333489 A1  Nov. 22, 2018

Related U.S. Application Data

(60) Provisional application No. 62/484,260, filed on Apr. 11, 2017, provisional application No. 62/524,927, filed on Jun. 26, 2017.

(51) Int. Cl.
| | | |
|---|---|---|
| *A61K 39/395* | (2006.01) | |
| *C07K 16/00* | (2006.01) | |
| *C07K 16/28* | (2006.01) | |
| *A61K 39/00* | (2006.01) | |
| *C07K 16/24* | (2006.01) | |

(52) U.S. Cl.
CPC .......... *A61K 39/3955* (2013.01); *C07K 16/00* (2013.01); *C07K 16/24* (2013.01); *C07K 16/2866* (2013.01); *A61K 2039/505* (2013.01); *A61K 2039/545* (2013.01); *C07K 2317/14* (2013.01); *C07K 2317/94* (2013.01)

(58) Field of Classification Search
CPC .......... A61K 39/3955; A61K 2039/505; C07K 16/00; C07K 16/2866; C07K 2317/94
See application file for complete search history.

(56) References Cited

U.S. PATENT DOCUMENTS

| | | | | |
|---|---|---|---|---|
| 8,883,979 | B2 * | 11/2014 | Ma ................... | A61K 39/39591 530/387.1 |
| 9,663,571 | B2 * | 5/2017 | Arnett ................ | C07K 16/248 |

FOREIGN PATENT DOCUMENTS

| | | |
|---|---|---|
| EP | 2526963 A1 | 11/2018 |
| WO | 2014194274 A2 | 12/2014 |
| WO | WO-2014194274 A2 * 12/2014 | ........... C07K 16/248 |

OTHER PUBLICATIONS

Borwankar et al., "Viscosity Reduction of a Concentrated Monoclonal Antibody with Arginine.HCl and Arginine. Glutamate", Industrial & Engineering Chemistry Research, 55(43) 2016.
Carayon "Highly concentrated formulations of Biotheurapeutics", MabDelivery—Labex Mabimprove Tours, Retrieved from the Internet on Jul. 24, 2017: http://mabdelivery.fr/medias/fichier/sophie-carayon-mabdelivery 1436434476023-pdf?INLINE=FALSE Jul. 2, 2015.
Fukuda et al., "Thermodynamic and Fluorescence Analyses to Determine Mechanisms of IgGl Stabilization and Destabilization by Arginine", Pharmaceutical Research, 31(4): 2014.
Goswami et al., "Developments and Challenges for mAb-Based Therapeutics", Antibodies, 2:452-500 (2013).
Kheddo et al., "The effect of arginine glutamate on the stability of monoclonal antibodies in solution", International Journal of Pharmaceutics, 473(1-2): 2014.
Mleczko et al., "Limitation of tuning the antibody-antigen reaction by changing the value of pH and its consequences for hyperthermia", Journal of Biochemistry, 156(4) 421-427 (2016).
Nema et al., "Key Formulation Challenges of protein (mAb) drugs", Retrieved from the Internet on Jun. 18, 2018: http://users.unimi.it/gazzalab/wordpress/wpcontent/uploads/2011/12/9-Key-formulation-challenges-of-protein-drugs.pdf Nov. 6, 2017.
Shire, "Formulation of proteins and monoclonal antibodies mAbs", Monoclonal Antibodies: Meeting the Challenges in Manufacturing, Formulation, Delivery and Stability of Final Drug Pro 2015.
Schneider, "Importance of isoelectric point (pI) of antibodies", The Antibody Society Sciences, https://www.antibodysociety.org/importance-isoelectric-point-pi-antibodies (2017).
Wang et al., "Antibody Structure, Instability, and Formulation", Journal of Pharmaceutical Sciences, 96(1): 1-26 (2007).

* cited by examiner

*Primary Examiner* — Ruixiang Li
(74) *Attorney, Agent, or Firm* — Proskauer Rose LLP; Fangli Chen; Julio J. Mendez

(57) ABSTRACT

The present invention provides, among other things, stable formulations comprising an anti-oncostatin M receptor (OSMR) antibody and having a pH ranging from approximately 6.0-7.6, wherein less than approximately 5% of the anti-OSMR antibody exists as high molecular weight (HMW) species in the formulation.

19 Claims, 9 Drawing Sheets
Specification includes a Sequence Listing.

Sample 1

| Test | Baseline | 1 mo | 3 mo | 1 mo | 3 mo |
|---|---|---|---|---|---|
| Storage Temperature | -70°C | -70°C | -70°C | 5°C | 5°C |
| pH | 6.7 | 6.7 | 6.6 | 6.6 | 6.6 |
| Protein concentration (mg/ml) | 201 | 211 | 182 | 209 | 186 |
| SEC (% aggregates) | <5% | <5% | <5% | <5% | <5% |
| CE-SDS (NR) (% monomer) | >90% | >90% | >90% | >90% | >90% |

Sample 2

| Test | Baseline | 0.5 mo | 1 mo | 3 mo | 0.5 mo | 1 mo | 3 mo |
|---|---|---|---|---|---|---|---|
| Storage Temperature | -70°C | -70°C | -70°C | -70°C | 5°C | 5°C | 5°C |
| pH | 6.7 | 6.8 | 6.7 | 6.6 | 6.8 | 6.7 | 6.6 |
| Protein concentration (mg/ml) | 178 | 178 | 185 | 177 | 179 | 183 | 171 |
| SEC (% aggregates) | <5% | <5% | <5% | <5% | <5% | <5% | <5% |
| CE-SDS (NR) (% monomer) | >90% | >90% | >90% | >90% | >90% | >90% | >90% |

FIGURE 8

Sample 3

| Test | Baseline | 0.5 mo | 1 mo | 3 mo | 0.5 mo | 1 mo | 3 mo |
|---|---|---|---|---|---|---|---|
| Storage Temperature | 25°C | 25°C | 25°C | 25°C | 40°C | 40°C | 40°C |
| pH | 6.8 | 6.6 | 6.6 | 6.6 | 6.7 | 6.6 | 6.6 |
| Protein concentration (mg/ml) | 187 | 200 | 184 | 181 | 195 | 171 | 180 |
| SEC (% aggregates) | <5% | <5% | <5% | <5% | <10% | <15% | <40% |
| CE-SDS (NR) (% monomer) | >90% | >90% | >90% | >90% | >90% | >90% | >80% |

Sample 4

| Test | Baseline | 0.5 mo | 1 mo | 3 mo | 0.5 mo | 1 mo | 3 mo |
|---|---|---|---|---|---|---|---|
| Storage Temperature | 25°C | 25°C | 25°C | 25°C | 40°C | 40°C | 40°C |
| pH | 6.7 | 6.8 | 6.7 | 6.6 | 6.8 | 6.7 | 6.68 |
| Protein concentration (mg/ml) | 178 | 180 | 179 | 173 | 177 | 185 | 170 |
| SEC (% aggregates) | <5% | <5% | <5% | <5% | <10% | <20% | <45% |
| CE-SDS (NR) (% monomer) | >90% | >90% | >90% | >90% | >90% | >90% | >80% |

FIGURE 9

STABLE ANTI-OSMR ANTIBODY FORMULATION

RELATED APPLICATIONS

This application claims priority to U.S. Provisional Application Ser. No. 62/484,260, filed Apr. 11, 2017, and Ser. No. 62/524,927, filed Jun. 26, 2017, the disclosures of which is hereby incorporated by reference.

SEQUENCE LISTING

The present specification makes reference to a Sequence Listing (submitted electronically as a .txt file named "KPL-002WO_SL" on Apr. 11, 2018). The .txt file was generated Apr. 10, 2018 and is 18,000 bytes in size. The entire contents of the Sequence Listing are herein incorporated by reference.

BACKGROUND

Developments in biotechnology have made it possible to produce a large variety of monoclonal antibodies for pharmaceutical applications. Because antibodies are larger and more complex than traditional organic and inorganic drugs, the formulation of such proteins poses special problems. One of the problems is the elevated viscosity values of antibody formulations, especially at high protein concentrations. Another problem is maintaining stability in antibody formulations, which is a critical concern for regulatory agencies. The delivery of high protein concentration is often required for subcutaneous administration due to volume limitations and dose requirements. Subcutaneous administration is an attractive route of delivery because it is less invasive for patients and reduces inconvenience and discomfort for them. Proteins tend to form viscous solutions at high concentration because of their macromolecular nature and potential for intermolecular interactions. Therefore, there is a need to develop stable antibody formulations as well as highly concentrated antibody formulations with viscosities at levels that facilitate the manufacture, preparation and administration of the antibody.

SUMMARY OF THE INVENTION

The present invention provides, among other thing, stable formulations for delivery of anti-oncostatin M receptor (OSMR) antibodies. In one aspect, the present invention provides stable formulations comprising an anti-oncostatin M receptor (OSMR) antibody and having a pH ranging from approximately 5.0-7.6, wherein less than approximately 5% of the anti-OSMR antibody exists as high molecular weight (HMW) species in the formulation. In one embodiment, the formulation of the invention is a stable, injectable formulation of an anti-oncostatin M receptor (OSMR) antibody, comprising: 75-250 mg/mL of the OSMR monoclonal antibody, 10-150 mM L-histidine, 10-150 mM L-Arginine Hydrochloride, 25-150 mM sodium chloride, 0.005%-0.5% (w/v) polysorbate 80 (PS80) at a pH 6.6-6.8; wherein the solution is isotonic, with an osmolarity ranging from 250-350 mOsm, and wherein at least 90% of the protein exist as stable intact monomeric IgG at about −70° C. or at about 5° C. for at least 1 month.

In one embodiment, less than 5%, 4%, 3%, 2%, 1%, or 0.5% of the anti-OSMR antibody exists as HMW species in the formulation. In one embodiment, the amount of HMW species in the formulation increases less than 5%, 4%, 3%, 2%, 1%, or 0.5% upon storage at 25° C. for more than 2 weeks. In one embodiment, upon storage at 25° C. for 4 weeks, the amount of HMW species in the formulation increases approximately between 0.3% to 0.7%, approximately between 0.3% to 0.6%, or approximately between 0.3% to 0.5%. In one embodiment, at least 90%, 92%, 94%, 95%, 96%, 97%, 98%, or 99% of the anti-OSMR antibody exists as monomer in the stable formulation. In one embodiment, the amount of monomer decreases less than 10%, 8%, 6%, 5%, 4%, 3%, 2%, 1%, or 0.5% upon storage at −70° C. for about 3 months, while greater than 90%, greater than 91%, greater than 92%, greater than 93%, greater than 94%, greater than 95%, greater than 96%, greater than 97%, greater than 98% or greater than 99% of the drug product exist as intact IgG monomer. In one embodiment, the antibody exihibits at least 95%, 96%, 97%, 98%, 99% or 100% antigen binding activity after storing at −70° C. for about 3 months. In one embodiment, the HMW species (% aggregates) do not increase more than 1%, or more than 1.5%, or more than 1.6%, or more than 1.7%, or more than 1.8%, or more than 1.9%, or more than 2%, or more than 3%, or more than 4%, or more than 5%, upon storage at −70° C. for about 3 months. In one embodiment, the amount of monomer decreases less than 10%, 8%, 6%, 5%, 4%, 3%, 2%, 1%, or 0.5% upon storage at 2-5° C. for about 3 months, while greater than 90%, greater than 91%, greater than 92%, greater than 93%, greater than 94%, greater than 95%, greater than 96%, greater than 97%, greater than 98% or greater than 99% of the drug product exist as intact IgG momomer. In one embodiment, the antibody exihibits at least 95%, 96%, 97%, 98%, 99% or 100% antigen binding activity after storing at 2-5° C. for about 3 months. In one embodiment, the HMW species (% agregates) do not increase more than 1%, or more than 1.5%, or more than 1.6%, or more than 1.7%, or more than 1.8%, or more than 1.9%, or more than 2%, or more than 3%, or more than 4%, or more than 5%, upon storage at 2-5° C. for about 3 months. In one embodiment, the HMW species, and/or the monomer are determined by size exclusion chromatography (SEC), analytical ultracentrifugation (AUC), field flow fractionation (FFF) or light scattering.

In one embodiment, the pH of the formulation ranges between approximately 5.0 to 7.6, between approximately 5.5 to 7.4, between approximately 5.8 to 7.2, between approximately 6.0 to 7.0, between approximately 6.1 to 7.1, between approximately 6.0 to 6.8, between approximately 6.0 to 6.6, between approximately 6.0 to 6.4, between approximately 6.4 to 7.6, between approximately 6.6 to 7.6, between approximately 6.8 to 7.6, between approximately 7.0 to 7.6, between approximately 6.6 to 6.8, between approximately 6.5 to 6.9, between approximately 6.4 to 6.9, or between approximately 7.2 to 7.6. In one embodiment, the pH of the formulation is approximately 6.2, 6.4, 6.5, 6.6, 6.7, 6.8, 6.9, 7.0, 7.2 7.4 or 7.6.

In one embodiment, the anti-OSMR antibody is present at a concentration of at least approximately 50 mg/mL. In one embodiment, the anti-OSMR antibody is present at a concentration of at least approximately 50 mg/mL, 75 mg/mL, 80 mg/mL, 85 mg/mL, 90 mg/mL, 100 mg/mL, 105 mg/mL, 110 mg/mL, 120 mg/mL, 125 mg/mL, 130 mg/mL, 135 mg/mL, 140 mg/mL, 145 mg/mL, 150 mg/mL, 155 mg/mL, 160 mg/mL, 170 mg/mL, 175 mg/mL, 180 mg/mL, 185 mg/mL, 190 mg/mL, 195 mg/mL, 200 mg/mL, 205 mg/mL, 210 mg/mL, 225 mg/mL, or 250 mg/mL.

In one embodiment, the anti-OSMR antibody has a pI ranging from 6.5-8.5. In one embodiment, the anti-OSMR antibody has a pI ranging from 7.0-8.0. In one embodiment, the anti-OSMR comprises one or more charged species, wherein the pI of the charged species ranges from 6.5-8.5. In one embodiment, the pI is determined by isoelectric focusing (IEF) or ion exchange chromatography (IEX).

In one embodiment, the formulation comprises one or more amino acids. In one embodiment, the one or more amino acids are present at a concentration between between 5 mM and 35 mM, between 10 mM and 35 mM, between 15 mM and 30 mM, 1 mM and 250 mM, between 10 mM and 250 mM, between 10 mM and 200 mM, between 10 mM and 150 mM or between 20 mM and 150 mM. In one embodiment, the one or more amino acids are selected from the group consisting of arginine, glutamic acid, glycine, histidine and combinations thereof. In one embodiment, the one or more amino acids comprise arginine. In one embodiment, arginine is selected from the group consisting of D-arginine and L-arginine, or combinations thereof. In one embodiment, the one or more amino acids do not include glutamic acid. In one embodiment, the amino acid is L-arginine. In one embodiment, arginine is present at a concentration between 20 mM and 30 mM, 15 mM and 35 mM, 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 25 mM and 150 mM. In one embodiment, arginine is present at a concentration of 25 mM. In one embodiment, the one or more amino acids comprise glutamic acid. In one embodiment, the one or more amino acids comprise arginine and glutamic acid. In one embodiment, the molar ratio of arginine to glutamic acid is at least 10:1, 5:1, 4:1, 3:1, 2:1, or 1:1. In one embodiment, glutamic acid is present at a concentration between 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 50 mM and 150 mM. In one embodiment, the one or more amino acids comprise histidine. In one embodiment, the amino acid is L-histidine. In one embodiment, the histidine is present at a concentration between 10 mM and 20 mM, between 15 mM and 25 mM, between 10 mM and 30 mM, between 5 mM and 25 mM, between 5 mM and 50 mM, between 5 mM and 75 mM, between 5 mM and 100 mM, between 5 mM and 125 mM, or between 5 mM and 150 mM. In one embodiment, histidine is present at concentration of 20 mM. In one embodiment, the one or more amino acids comprise glycine. In one embodiment, the glycine is present at a concentration between 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 150 mM and 200 mM.

In one embodiment, the formulation further comprises a buffer. In one embodiment, the buffer is selected from the group consisting of citrate, phosphate, succinate, histidine, and combinations thereof. In one embodiment, the buffer is phosphate. In one embodiment, the buffer is present at a concentration between 1 mM and 100 mM, between 5 mM and 75 mM, between 5 mM and 50 mM, between 5 mM and 40 mM, between 5 mM and 30 mM, between 5 mM and 25 mM, or between 10 mM to 20 mM.

In one embodiment, the formulation further comprises a salt. In one embodiment, the salt comprises a halide. In one embodiment, the halide is an alkali metal halide. In one embodiment, the salt is NaCl. In one embodiment, NaCl is present at a concentration between 25 mM and 250 mM, between 25 mM and 200 mM, between 25 mM and 175 mM, between 50 mM and 200 mM, between 50 mM and 175 mM, between 50 mM and 150 mM, between 120 mM and 130 mM, between 125 mM and 135 mM or between 75 mM and 150 mM. In one embodiment, NaCl is present at a concentration of 125 mM. In one embodiment, the molar ratio of NaCl to arginine is at least 1:1, 1.5:1, 3:1, or 5:1. In one embodiment, the molar ratio of NaCl to arginine is approximately 5:1. In another embodiment, the molar ratio of NaCl to histidine is approximately 6:1.

In another aspect, the present invention provides stable formulations comprising an anti-oncostatin M receptor (OSMR) antibody at a concentration of at least 50 mg/mL, at least 100 mg/mL, or at least 150 mg/mL, and, in each case, having a pH ranging from approximately 6.0-7.6, wherein the anti-OSMR antibody has a pI ranging from approximately 6.5-8.5. In one embodiment, the pH of the formulation ranges between approximately 6.0 to 7.6, between approximately 6.0 to 7.4, between approximately 6.0 to 7.2, between approximately 6.0 to 7.0, between approximately 6.5 to 7.1, between approximately 6.0 to 6.8, between approximately 6.0 to 6.6, between approximately 6.0 to 6.4, between approximately 6.4 to 7.6, between approximately 6.6 to 7.6, between approximately 6.8 to 7.6, between approximately 7.0 to 7.6, or between approximately 7.2 to 7.6. In one embodiment, the anti-OSMR antibody is present at a concentration of at least 150 mg/mL, having a pH ranging from approximately 6.6 to 6.8 and a pI ranging from approximately 7.2 to 8.0.

In one embodiment, the anti-OSMR antibody is present at a concentration of at least approximately 75 mg/mL, 100 mg/mL, 125 mg/mL, 150 mg/mL, 175 mg/mL, 200 mg/mL, 225 mg/mL, or 250 mg/mL. In one embodiment, the anti-OSMR antibody is present at a concentration between approximately 50 mg/mL and 250 mg/mL, between approximately 75 mg/mL and 250 mg/mL, between approximately 100 mg/mL and 250 mg/mL, between approximately 125 mg/mL and 250 mg/mL, between approximately 150 mg/mL and 250 mg/mL, between approximately 175 mg/mL and 250 mg/mL, between approximately 50 mg/mL and 225 mg/mL, between approximately 50 mg/mL and 200 mg/mL, between approximately 50 mg/mL and 175 mg/mL, between approximately 50 mg/mL and 150 mg/mL, between approximately 50 mg/mL and 125 mg/mL, between approximately 50 mg/mL and 100 mg/mL, between approximately 150 mg/mL and 230 mg/mL, or between approximately 150 mg/mL and 250 mg/mL.

In one embodiment, the anti-OSMR antibody has a pI ranging from 6.5-8.5, 7.2-8.0 or from 7.0-8.0.

In one embodiment, the formulation comprises salt. In one embodiment, the salt comprises a halide. In one embodiment, the halide is an alkali metal halide. In one embodiment, the salt is NaCl. In one embodiment, NaCl is present at a concentration between 25 mM and 250 mM, between 25 mM and 200 mM, between 25 mM and 175 mM, between 50 mM and 200 mM, between 50 mM and 175 mM, between 50 mM and 150 mM, between 120 mM and 130 mM, between 125 mM and 135 mM or between 75 mM and 150 mM.

In one embodiment, the formulation comprises one or more amino acids. In one embodiment, the one or more amino acids are present at a concentration between 5 mM and 35 mM, between 10 mM and 35 mM, between 15 mM and 30 mM, between 1 mM and 250 mM, between 10 mM and 250 mM, between 10 mM and 200 mM, between 10 mM and 150 mM or between 20 mM and 150 mM. In one embodiment, the one or more amino acids are selected from the group consisting of arginine, glutamic acid, glycine, histidine and combinations thereof. In one embodiment, the one or more amino acids comprise arginine. In one embodiment, the one or more amino acids do not include glutamic acid. In one embodiment, arginine is present at a concentration between 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 25 mM and 150 mM. In one embodiment, the one or more amino acids comprise glutamic acid. In one embodiment, the one or more amino acids comprise arginine and glutamic acid. In one embodiment, the molar ratio of arginine to glutamic acid is at least 10:1, 5:1, 4:1, 3:1, 2:1, or 1:1. In one embodiment, glutamic acid is present at a concentration between 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 50 mM and 150 mM. In one embodiment, the molar ratio of NaCl to arginine is at least 1:1, 1.5:1, 3:1, or 5:1. In one embodiment, the one or more amino acids comprise histidine. In one embodiment, the histidine is present at a concentration between 10 mM and 20 mM, between 5 mM and 25 mM, between 5 mM and 50 mM, between 5 mM and 75 mM, between 5 mM and 100 mM, between 5 mM and 125 mM, or between 5 mM and 150 mM. In one embodiment, the one or more amino acids comprise glycine. In one embodiment, the glycine is present at a concentration between 10 mM and 250 mM, between 10 mM and 200 mM, between 10 mM and 150 mM, between 10 mM and 125 mM, between 10 mM and 100 mM, between 10 mM and 75 mM, between 10 mM and 50 mM, or between 150 mM and 200 mM.

In one embodiment, the formulation further comprises a buffer. In one embodiment, the buffer is selected from the group consisting of citrate, phosphate, succinate, histidine and combinations thereof. In one embodiment, the buffer is phosphate. In one embodiment, the buffer is present at a concentration between 1 mM and 100 mM, between 5 mM and 75 mM, between 5 mM and 50 mM, between 5 mM and 40 mM, between 5 mM and 30 mM, between 5 mM and 25 mM, or between 10 mM to 20 mM. In one embodiment, the anti-OSMR antibody is present in a stable, injectable formulation, comprising: 50-250 mg/mL of the OSMR monoclonal antibody, 10-150 mM L-histidine, 10-150 mM L-Arginine Hydrochloride, 25-150 mM sodium chloride, 0.005%-0.5% (w/v) polysorbate 80 (PS80) at a pH 6.6-6.8. The stable, injectable formulation comprises an isotonic solution. In some embodiments, the formulation buffer comprises 20 mM L-Histidine, 25 mM L-Arginine-HCl, 125 mM NaCl, 0.05% (w/v) PS80, pH 6.6-6.8. In one embodiment, 75-250 mg/mL anti-OSMR antibody is present in a stable, injectable formulation comprising 20 mM L-Histidine, 25 mM L-Arginine-HCl, 125 mM NaCl, 0.05% (w/v) PS80, pH 6.6-6.8. In one embodiment, the injectable formulation comprises an osmolarity ranging between 250 and 350 mOsm. In one embodiment, the osmolarity of the formulation is between 270 and 300 mOsm. The stable formulation comprising the anti-OSMR antibody has a pI ranging from 6.5-8.5. In one embodiment, the stable formulation comprising the anti-OSMR antibody has a pI ranging from 7.0 to 8.0. In one embodiment, the stable formulation comprising the anti-OSMR antibody has a pI ranging from 7.2 to 8.0. In one embodiment, the stable formulation comprising the anti-OSMR antibody comprises one or more charged species, wherein the pI of the charged species ranges from 6.5 to 8.5.

In one embodiment, the formulation has a viscosity of less than 50 mPa*s measured by a microfluidic rheometer. In one embodiment, the formulation has a viscosity of less than 30 mPa*s measured by a microfluidic rheometer. In one embodiment, the formulation has a viscosity of less than 20 mPa*s measured by a microfluidic rheometer. In one embodiment, the formulation has a viscosity of less than 15 mPa*s measured by a microfluidic rheometer. In one embodiment, the formulation has a viscosity, as measured by a microfluidic rheometer, between approximately 1 and 30 mPa*s, between approximately 2 and 28 mPa*s, between approximately 4 and 30 mPa*s, between approximately 6 and 30 mPa*s, between approximately 8 and 30 mPa*s, between approximately 10 and 30 mPa*s, between approximately 12 and 30 mPa*s, between approximately 14 and 30 mPa*s, between approximately 16 and 30 mPa*s, between approximately 18 and 30 mPa*s, between approximately 20 and 30 mPa*s, between approximately 22 and 30 mPa*s, between approximately 24 and 30 mPa*s, between approximately 26 and 30 mPa*s, or between approximately 28 and 30 mPa*s. In one embodiment, the formulation has a shear rate of less than 1000 $s^{-1}$ at 25° C.

In one embodiment, the formulation is a liquid formulation. In one embodiment, the formulation is reconstituted from a lyophilized powder.

In one embodiment, the formulation can be expelled via a 27G ½" needle with 6.5 pound-force or less at an injection rate of 0.1 mL/second at about 25° C. In one embodiment, the formulation is easily injectable.

In one embodiment, the anti-OSMR antibody comprises a light chain complementary-determining region 1 (LCDR1) defined by SEQ ID NO: 8, a light chain complementary-determining region 2 (LCDR2) defined by SEQ ID NO: 9, and a light chain complementary-determining region 3 (LCDR3) defined by SEQ ID NO: 10; and a heavy chain complementary-determining region 1 (HCDR1) defined by SEQ ID NO: 5, a heavy chain complementary-determining region 2 (HCDR2) defined by SEQ ID NO: 6, and a heavy chain complementary-determining region 3 (HCDR3) defined by SEQ ID NO: 7. In one embodiment, the anti-OSMR antibody comprises a light chain variable domain having an amino acid sequence at least 90% identical to SEQ ID NO: 4 a heavy chain variable domain having an amino acid sequence at least 90% identical to SEQ ID NO: 3. In one embodiment, the light chain variable domain has the amino acid sequence set forth in SEQ ID NO: 4 and the heavy chain variable domain has the amino acid sequence set forth in SEQ ID NO: 3. In one embodiment, the anti-OSMR antibody comprises CH1, hinge and CH2 domains derived from an IgG4 antibody fused to a CH3 domain derived from an IgG1 antibody. In one embodiment, the anti-OSMR antibody comprises a light chain having an amino acid sequence at least 90% identical to SEQ ID NO: 2 and a heavy chain having an amino acid sequence at least 90% identical to SEQ ID NO: 1. In one embodiment, the light chain has the amino acid sequence set forth in SEQ ID NO: 2 and the heavy chain has the amino acid sequence set forth in SEQ ID NO: 1.

In another aspect, the present invention provides stable formulations comprising an antibody at a concentration of at least 50 mg/mL and arginine, wherein the arginine is present at an amount greater than any non-arginine amino acid in the formulation. In one embodiment, the formulation does not comprise glutamic acid. In one embodiment, the formulation comprises glutamic acid. In one embodiment, the molar ratio of arginine to glutamic acid is at least 10:1, 5:1, 4:1, 3:1, 2:1, or 1:1. In one embodiment, the amino acid is L-arginine.

In one embodiment, the formulation of the anti-OSMR antibody comprising a light chain having an amino acid sequence at least 90% identical to SEQ ID NO: 2 and a heavy chain having an amino acid sequence at least 90% identical to SEQ ID NO: 1 comprises 20 mM L-Histidine, 25 mM L-Arginine-HCl, 125 mM NaCl, 0.05% (w/v) PS80, pH 6.6-6.8. In one embodiment, the formulation of the anti-OSMR antibody comprising a light chain variable domain having an amino acid sequence at least 90% identical to SEQ ID NO: 4 a heavy chain variable domain having an amino acid sequence at least 90% identical to SEQ ID NO: 3 comprises 20 mM L-Histidine, 25 mM L-Arginine-HCl, 125 mM NaCl, 0.05% (w/v) PS80, pH 6.6-6.8. In one embodiment, the formulation of the anti-OSMR antibody comprising the light chain variable domain having the amino acid sequence set forth in SEQ ID NO: 4 and the heavy chain variable domain having the amino acid sequence set forth in SEQ ID NO: 3 comprises 20 mM L-Histidine, 25 mM L-Arginine-HCl, 125 mM NaCl, 0.05% (w/v) PS80, pH 6.6-6.8. In one embodiment, the formulation of the anti-OSMR antibody comprising the light chain has the amino acid sequence set forth in SEQ ID NO: 2 and the heavy chain has the amino acid sequence set forth in SEQ ID NO: 1 comprises 20 mM L-Histidine, 25 mM L-Arginine-HCl, 125 mM NaCl, 0.05% (w/v) PS80, pH 6.6-6.8.

In another aspect, the present invention provides methods of treating a disease, disorder or condition associated with OSMR comprising administering into a subject in need of treatment any stable formulation described above. In one embodiment, the formulation is administered intravenously. In one embodiment, the formulation is administered subcutaneously. In one embodiment, the disease, disorder or condition associated with OSMR is selected from pruritus, atopic dermatitis, inflammation, pain, prurigo nodularis, dermatitis, asthma, autoimmune disease, paraneoplastic autoimmune diseases, cartilage inflammation, fibrosis (including, but not limited to, pulmonary fibrosis and skin fibrosis), fibrotic disease, chronic obstructive pulmonary disease (COPD), interstitial pneumonitis, abnormal collagen deposition, systemic cutaneous amyloidosis, primary cutaneous amyloidosis, Behcet's disease, nasal polyposis, liver cirrhosis, cartilage degradation, bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, scleroderma-associated interstitial lung disease, vasculitis, myolitis, polymyolitis, dermatomyolitis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophagitis, eosinophilic bronchitis, bronchitis, Guillain-Barre disease, Type I diabetes mellitus, thyroiditis (e.g., Graves' disease), Addison's disease, Reynaud's phenomenon, autoimmune hepatitis, GVHD, transplantation rejection, kidney damage, cardiovascular disease, infection, sepsis, HIV infection, trauma, kidney allograft nephropathy, IgA nephropathy, diabetic nephropathy, diabetic retinopathy, macular degeneration, biliary atresia, congestive heart failure, atherosclerosis, restenosis, radiation-induced fibrosis, chemotherapy-induced fibrosis, burns, surgical trauma, and glomerulosclerosis.

In another aspect, the present invention provides methods for treating pruritus comprising subcutaneously administering to a subject in need of treatment a formulation comprising an anti-oncostatin M receptor (OSMR) antibody at a concentration of at least 50 mg/mL. In one embodiment, the anti-OSMR antibody is present at a concentration of at least approximately 75 mg/mL, 80 mg/mL, 90 mg/mL, 100 mg/mL, 105 mg/mL, 110 mg/mL, 120 mg/mL, 125 mg/mL, 130 mg/mL, 135 mg/mL, 140 mg/mL, 145 mg/mL, 150 mg/mL, 155 mg/mL, 160 mg/mL, 170 mg/mL, 175 mg/mL, 180 mg/mL, 185 mg/mL, 190 mg/mL, 200 mg/mL, 205 mg/mL, 210 mg/mL, 215 mg/mL, 220 mg/mL, 225 mg/mL, or 250 mg/mL. In one embodiment, the anti-OSMR antibody is present at a concentration between approximately 50 mg/mL and 250 mg/mL, between approximately 75 mg/mL and 250 mg/mL, between approximately 100 mg/mL and 250 mg/mL, between approximately 125 mg/mL and 250 mg/mL, between approximately 150 mg/mL and 250 mg/mL, between approximately 175 mg/mL and 250 mg/mL, between approximately 50 mg/mL and 225 mg/mL, between approximately 50 mg/mL and 200 mg/mL, between approximately 50 mg/mL and 175 mg/mL, between approximately 50 mg/mL and 150 mg/mL, between approximately 50 mg/mL and 125 mg/mL, or between approximately 50 mg/mL and 100 mg/mL, or between approximately 150 mg/mL and 250 mg/mL.

In one embodiment, the anti-OSMR antibody comprises a light chain complementary-determining region 1 (LCDR1) defined by SEQ ID NO: 8, a light chain complementary-determining region 2 (LCDR2) defined by SEQ ID NO: 9, and a light chain complementary-determining region 3 (LCDR3) defined by SEQ ID NO: 10; and a heavy chain complementary-determining region 1 (HCDR1) defined by SEQ ID NO: 5, a heavy chain complementary-determining region 2 (HCDR2) defined by SEQ ID NO: 6, and a heavy chain complementary-determining region 3 (HCDR3) defined by SEQ ID NO: 7. In one embodiment, the anti-OSMR antibody comprises a light chain variable domain having an amino acid sequence at least 90% identical to SEQ ID NO: 4 and a heavy chain variable domain having an amino acid sequence at least 90% identical to SEQ ID NO: 3. In one embodiment, the light chain variable domain has the amino acid sequence set forth in SEQ ID NO: 4 and the heavy chain variable domain has the amino acid sequence set forth in SEQ ID NO: 3. In one embodiment, the anti-OSMR antibody comprises CH1, hinge and CH2 domains derived from an IgG4 antibody fused to a CH3 domain derived from an IgG1 antibody. In one embodiment, the anti-OSMR antibody comprises a light chain having an amino acid sequence at least 90% identical to SEQ ID NO: 2 and a heavy chain having an amino acid sequence at least 90% identical to SEQ ID NO: 1. In one embodiment, the light chain has the amino acid sequence set forth in SEQ ID NO: 2; and the heavy chain has the amino acid sequence set forth in SEQ ID NO: 1.

In one embodiment, the formulation is administered in a volume of less than 5 mL, 4 mL, 3 mL, or 2 mL. In one embodiment, the formulation has a viscosity of less than 50 mPa*s, less than 30 mPa*s, less than 20 mPa*s, or less than 15 mPa*s as measured by a microfluidic rheometer. In one embodiment, the formulation has a viscosity, as measured by a microfluidic rheometer, between approximately 1 and 30 mPa*s, between approximately 2 and 28 mPa*s, between approximately 4 and 30 mPa*s, between approximately 6 and 30 mPa*s, between approximately 8 and 30 mPa, between approximately 10 and 30 mPa*s, between approximately 12 and 30 mPa*s, between approximately 14 and 30 mPa*s, between approximately 16 and 30 mPa*s, between approximately 18 and 30 mPa*s, between approximately 20 and 30 mPa*s, between approximately 22 and 30 mPa*s, between approximately 24 and 30 mPa*s, between approximately 26 and 30 mPa*s, or between approximately 28 and 30 mPa*s. In one embodiment, the formulation has a shear rate of less than 1000 $s^{-1}$ at 25° C.

In one embodiment, less than 5%, 4%, 3%, 2%, 1%, or 0.5% of the anti-OSMR antibody exists as HMW species in the formulation. In one embodiment, the amount of HMW species in the formulation increases less than 5%, 4%, 3%, 2%, 1%, or 0.5% upon storage at 25° C. for 2 weeks or more. In one embodiment, the amount of HMW species in the formulation increases less than 5%, 4%, 3%, 2%, 1%, or 0.5% upon storage at 25° C. for 4 weeks or more. In one embodiment, the amount of HMW species in the formulation increases less than 5%, 4%, 3%, 2%, 1%, or 0.5% upon storage at 25° C. for 3 months or more. In one embodiment, upon storage at 25° C. for 4 weeks, the amount of HMW species in the formulation increases approximately between 0.3% and 0.7%, approximately between 0.3% and 0.6%, or approximately between 0.3% and 0.5%. In one embodiment, the formulation is stable upon storage at about 25° C. for 3 months, and the amount of HMW species in the formulation increases approximately between 0.3% to 5%, approximately between 0.3% to 3%, or approximately between 0.3% to 2.5%. In one embodiment, the formulation is stable upon storage at about 25° C. for 3 months, and the percent of intact IgG monomer is above 90% of the total protein content.

In one embodiment, the formulation is stable through multiple freeze-thaw cycles. In one embodiment, the formulation is stable in storage at about 25° C. the amount of intact IgG is above 90% after multiple freeze-thaw cycles and storage for at least 3 months, or at least 6 months or at least 12 months or at least 24 months. In one embodiment, the formulation is stable in storage at 2-5° C. for at least 3 months, or for at least 6 months, or for at least 1 year, or for at least 2 years, or for at least 3 years, or for at least 4 years, or for at least 5 years, or, for at least 10 years. In one embodiment, the formulation is stable in storage at −70° C. for at least 3 months, for at least 6 months, for at least 1 year, for at least 2 years, for at least 3 years, for at least 4 years, for at least 5 years, or, for at least 10 years.

BRIEF DESCRIPTION OF THE DRAWING

The drawings are for illustration purposes only not for limitation.

FIG. 8 depicts characteristics of the exemplary formulation samples when stored over a period of three months at −70° C. and at 5° C.

FIG. 9 depicts characteristics of the exemplary formulation samples when stored over a period of three months at 25±2° C. (accelerated conditions) and at 40±2° C. (stressed) conditions.

DEFINITIONS

Figure 1:
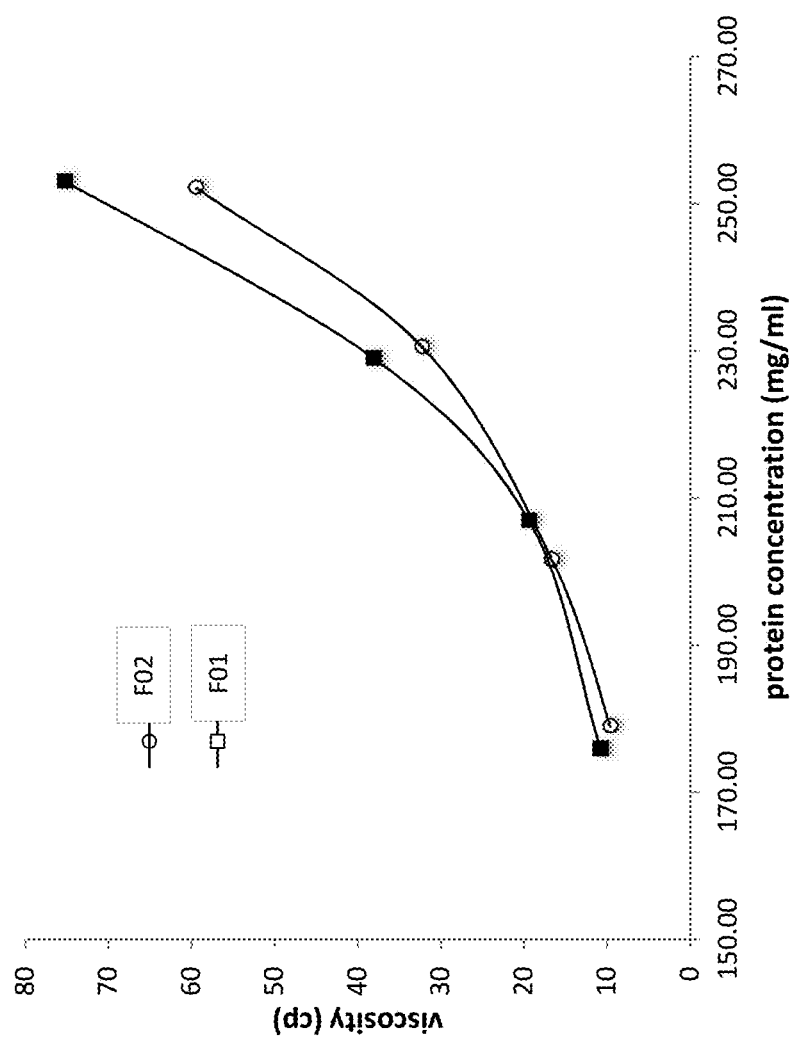
FIG. 1 depicts an exemplary graph illustrating the effect of protein concentration on viscosity in two different formulations of anti-OSMR antibody.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, term "amino acid," in its broadest sense, refers to any compound and/or substance that can be incorporated into a polypeptide chain. In some embodiments, an amino acid has the general structure $H_2N$—C(H)(R)—COHO. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Delivery: As used herein, the term "delivery" encompasses both local and systemic delivery.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles. For the purpose of the present application, the term high molecular weight species (HMW) of the product and "aggregates" are used interchangeably.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLAS TN for nucleotide sequences and BLASTP, gapped BLAST, and PSI-BLAST for amino acid sequences. Exemplary such programs are described in Altschul, et al., Basic local alignment search tool, *J Mal. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suitable for subcutaneous delivery: As used herein, the phrase "suitable for subcutaneous delivery" or "formulation for subcutaneous delivery" as it relates to the pharmaceutical compositions of the present invention generally refers to the stability, viscosity, and solubility properties of such compositions, as well as the ability of such compositions to deliver an effective amount of antibody contained therein to the targeted site of delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease or disorder to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, stable formulations comprising an anti-Oncostatin M Receptor β (OSMR) antibody and having a pH ranging from approximately 6.0-7.6, wherein less than 5% of the anti-OSMR antibody exists as high molecular weight (HMW) species in the formulation. Also provided are stable formulations comprising an anti-OSMR antibody having a pH ranging from approximately 6.0-7.6, wherein the anti-OSMR antibody has a pI ranging from about 6.5-8.5. In some embodiments, the formulation comprises arginine and, optionally, NaCl. In some embodiments, the formulation is suitable for subcutaneous delivery. In some embodiments, stable formulations of the present invention are suitable for treating pruritus or other diseases and disorders associated with OSMR.

Various aspects of the invention are described in detail in the following sections. The use of sections is not meant to limit the invention. Each section can apply to any aspect of the invention. In this application, the use of "or" means "and/or" unless stated otherwise.

Anti-Oncostatin M Receptor (OSMR) Antibodies

In some embodiments, inventive compositions and methods provided by the present invention are used to deliver an anti-OSMR antibody to a subject in need. In certain embodiments of the invention, the anti-OSMR antibodies are fully-human monoclonal antibodies that specifically inhibit IL-31 and oncostatin M (OSM)-induced activation of the IL-31 receptor and type II OSM receptor, respectively, through binding to OSMR, the subunit common to both receptors. The antibody is comprised of two light chains and two heavy chains. In some embodiments, the light chain contains a lambda constant region. The constant regions of the heavy chain contain the CH1, hinge, and CH2 domains of a human immunoglobulin IgG4 antibody fused to the CH3 domain of a human IgG1 antibody. In other embodiments, the heavy chain of the anti-OSMR antibody contains a S228P modification to improve stability and a N297Q modification to remove an N-linked glycosylation site.

```
Anti-OSMR Heavy Chain Amino Acid Sequence
                                     (SEQ ID NO: 1)
QVQLVQSGAEVKKPGASVKVSCKASGYTFTSYEINWVRQATGQGLEWMGW

MNPNSGYTGYAQKFQGRVTMTRDTSISTAYMEMSSLRSEDTAVYYCARDI

VAANTDYYFYYGMDVWGQGTTVTVSSASTKGPSVFPLAPCSRSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREE

QFQSTYRVVSVLTVLHQDWLNGKEYKCKVSNKGLPSSIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PG

Anti-OSMR Light Chain Amino Acid Sequence
                                     (SEQ ID NO: 2)
QSVLTQPPSASGTPGQRVTISCSGSNSNIGSNTVNWYHQLPGTAPKLLIY

NINKRPSGVPDRFSGSKSGSSASLAISGLQSEDEADYYCSTWDDSLDGVV

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS

Anti-OSMR Heavy Chain Variable Domain Amino Acid
Sequence
                                     (SEQ ID NO: 3)
QVQLVQSGAEVKKPGASVKVSCKASGYTFTSYEINWVRQATGQGLEWMGW

MNPNSGYTGYAQKFQGRVTMTRDTSISTAYMEMSSLRSEDTAVYYCARDI

VAANTDYYFYYGMDVWGQGTTVTVSS
```

-continued

Anti-OSMR Light Chain Variable Domain Amino Acid
Sequence
(SEQ ID NO: 4)
QSVLTQPPSASGTPGQRVTISCSGSNSNIGSNTVNWYHQLPGTAPKLLIY

NINKRPSGVPDRFSGSKSGSSASLAISGLQSEDEADYYCSTWDDSLDGVV

FGGGTKLTVLG

Anti-OSMR Heavy Chain Variable Domain CDR 1
(HCDR1) Amino Acid Sequence
(SEQ ID NO: 5)
SYEIN Anti-OSMR Heavy Chain Variable Domain CDR 2
(HCDR2) Amino Acid Sequence
(SEQ ID NO: 6)
WMGWMNPNSGYTGYAQKFQGR Anti-OSMR Heavy Chain Variable Domain CDR 3
(HCDR3) Amino Acid Sequence
(SEQ ID NO: 7)
DIVAANTDYYFYYGMDV Anti-OSMR Light Chain Variable Domain CDR1
(LCDR1) Amino Acid Sequence
(SEQ ID NO: 8)
SGSNSNIGSNTVN Anti-OSMR Light Chain Variable Domain CDR2
(LCDR2) Amino Acid Sequence
(SEQ ID NO: 9)
NINKRPS Anti-OSMR Light Chain Variable Domain CDR3
(LCDR3) Amino Acid Sequence
(SEQ ID NO: 10)
STWDDSLDGVV Anti-OSMR Heavy Chain Signal Peptide Amino
Acid Sequence
(SEQ ID NO: 11)
MDFGLSLVFLVLILKGVQC Anti-OSMR Light Chain Signal Peptide Amino
Acid Sequence
(SEQ ID NO: 12)
MATGSRTSLLLAFGLLCLSWLQEGSA Anti-OSMR Heavy Chain Amino Acid Sequence -
IgG4 CH1, Hinge, and CH2 Domains
(SEQ ID NO: 13)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFQSTYRVVSVLTVLHQDWLNGKEYK

CKVSNKGLPSSIEKTISKAK

Anti-OSMR Heavy Chain Amino Acid Sequence -
IgG1 CH3 Domain
(SEQ ID NO: 14)
GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPG

Anti-OSMR Heavy Chain Amino Acid Sequence -
Constant Domain
(SEQ ID NO: 15)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

-continued
PEVQFNWYVDGVEVHNAKTKPREEQFQSTYRVVSVLTVLHQDWLNGKEYK

CKVSNKGLPSSIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG

Anti-OSMR Light Chain Amino Acid Sequence -
IgG Lambda Constant Domain
(SEQ ID NO: 16)
QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS

In some embodiments of the invention, an anti-OSMR antibody comprises a light chain complementary-determining region 1 (LCDR1) defined by SEQ ID NO: 8, a light chain complementary-determining region 2 (LCDR2) defined by SEQ ID NO: 9, and a light chain complementary-determining region 3 (LCDR3) defined by SEQ ID NO: 10; and a heavy chain complementary-determining region 1 (HCDR1) defined by SEQ ID NO: 5, a heavy chain complementary-determining region 2 (HCDR2) defined by SEQ ID NO: 6, and a heavy chain complementary-determining region 3 (HCDR3) defined by SEQ ID NO: 7.

In some embodiments of the invention, an anti-OSMR antibody comprises CDR amino acid sequences with at least 75%, 80%, 85%, 90%, 91%, 92%, 93%, 94%, 95%, 96%, 97%, 98%, 99% or more identity with one or more of SEQ ID NO: 8, SEQ ID NO: 9, SEQ ID NO: 10, SEQ ID NO: 5, SEQ ID NO: 6, and SEQ ID NO: 7.

In some embodiments of the invention, an anti-OSMR antibody comprises a light chain variable domain having an amino acid sequence at least 90% identical to SEQ ID NO: 4 and a heavy chain variable domain having an amino acid sequence at least 90% identical to SEQ ID NO: 3. In some embodiments of the invention, an anti-OSMR antibody has a light chain variable domain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 4 and a heavy chain variable domain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 3. In some embodiments of the invention, an anti-OSMR antibody comprises a light chain variable domain that has the amino acid sequence set forth in SEQ ID NO: 4 and a heavy chain variable domain that has the amino acid sequence set forth in SEQ ID NO: 3.

In some embodiments of the invention, an anti-OSMR antibody comprises a light chain having an amino acid sequence at least 90% identical to SEQ ID NO: 2 and a heavy chain having an amino acid sequence at least 90% identical to SEQ ID NO: 1. In some embodiments of the invention, an anti-OSMR antibody has a light chain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 2 and a heavy chain amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 1. In some embodiments of the invention, an anti-OSMR antibody comprises a light chain that has the amino acid sequence set forth in SEQ ID NO: 2 and a heavy chain that has the amino acid sequence set forth in SEQ ID NO: 1.

In some embodiments of the invention, a heavy chain constant region of an anti-OSMR antibody comprises CH1, hinge and CH2 domains derived from an IgG4 antibody fused to a CH3 domain derived from an IgG1 antibody. In some embodiments, the CH1, hinge and CH2 domains derived from an IgG4 antibody comprise SEQ ID NO: 13. In some embodiments, the CH3 domain derived from an IgG1 antibody comprises SEQ ID NO: 14. In some embodiments, the heavy chain constant region of an anti-OSMR antibody according to the present invention comprises an amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 13. In some embodiments, the heavy chain constant region of an anti-OSMR antibody according to the present invention comprises an amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 14. In some embodiments, the heavy chain constant region of an anti-OSMR antibody according to the present invention comprises an amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 15. In some embodiments, an anti-OSMR antibody according to the present invention comprises a lambda constant domain derived from an IgG antibody. In some embodiments, the lambda constant domain derived from an IgG comprises SEQ ID NO: 16. In some embodiments, an anti-OSMR antibody according to the present invention comprises an amino acid sequence with at least 50%, 55%, 60%, 65%, 70%, 75%, 80%, 85%, 90%, 91%, 92%, 93%, 94%, 95%, 96%, 97%, 98%, 99% or more identity to SEQ ID NO: 16.

Formulations

Exemplary formulations of the present invention are described herein. Formulations of the present invention comprise anti-OSMR antibodies as described above. In some embodiments, formulations are stable formulations for subcutaneous delivery. Among other things, formulations described herein are capable of solubilizing high concentrations of anti-OSMR antibody and are suitable for subcutaneous, intradermal, intramuscular and/or intra-articular delivery.

In some embodiments of the invention, a formulation comprises an anti-OSMR antibody at a concentration of at least approximately 50 mg/mL. In some embodiments of the invention, a formulation comprises an anti-OSMR antibody at a concentration of at least approximately 60 mg/mL. In some embodiments of the invention, a formulation comprises an anti-OSMR antibody at a concentration of at least approximately 70 mg/mL. In some embodiments of the invention, a formulation comprises an anti-OSMR antibody at a concentration of at least approximately 80 mg/mL. In some embodiments of the invention, a formulation comprises an anti-OSMR antibody at a concentration of at least approximately 90 mg/mL. In some embodiments of the invention, a formulation comprises an anti-OSMR antibody at a concentration of at least approximately 100 mg/mL. In some embodiments of the invention, a formulation comprises an anti-OSMR antibody at a concentration of at least approximately 110 mg/mL. In some embodiments of the invention, a formulation comprises an anti-OSMR antibody at a concentration of at least approximately 120 mg/mL. In some embodiments of the invention, a formulation comprises an anti-OSMR antibody at a concentration of at least approximately 130 mg/mL. In some embodiments of the invention, a formulation comprises an anti-OSMR antibody at a concentration of at least approximately 140 mg/mL. In some embodiments of the invention, a formulation comprises an anti-OSMR antibody at a concentration of at least approximately 150 mg/mL. In some embodiments of the invention, a formulation comprises an anti-OSMR antibody at a concentration of at least approximately 160 mg/mL. In some embodiments of the invention, a formulation comprises an anti-OSMR antibody at a concentration of at least approximately 170 mg/mL. In some embodiments of the invention, a formulation comprises an anti-OSMR antibody at a concentration of at least approximately 180 mg/mL. In some embodiments of the invention, a formulation comprises an anti-OSMR antibody at a concentration of at least approximately 190 mg/mL. In some embodiments of the invention, a formulation comprises an anti-OSMR antibody at a concentration of at least approximately 200 mg/mL. In some embodiments of the invention, a formulation comprises an anti-OSMR antibody at a concentration of at least approximately 210 mg/mL. In some embodiments of the invention, a formulation comprises an anti-OSMR antibody at a concentration of at least approximately 220 mg/mL. In some embodiments of the invention, a formulation comprises an anti-OSMR antibody at a concentration of at least approximately 230 mg/mL. In some embodiments of the invention, a formulation comprises an anti-OSMR antibody at a concentration of at least approximately 240 mg/mL. In some embodiments of the invention, a formulation comprises an anti-OSMR antibody at a concentration of at least approximately 250 mg/mL. In some embodiments, the formulation comprises about 180 mg/ml anti-OSMR antibody.

In some embodiments, the formulation prior to packaging or filling comprises about 5% more drug substance than the concentration intended in the final product formulation (the target concentration). Upon packaging or filling of the drug product, the formulation comprising about 5% more drug substance is diluted to the target concentration with placebo, i.e., the same formulation buffer, but lacking drug substance (e.g. 20 mM L-Histidine, 25 mM L-Arginine HCl, 125 mM NaCl, 0.05% (w/v) PS80, pH 6.6-6.8)

Amino Acids

In some embodiments of the invention, a formulation comprises one or more amino acids. In some embodiments, the one or more amino acids are present at a concentration between 10 mM and 250 mM. In some embodiments, the one or more amino acids are present at a concentration between 10 mM and 225 mM. In some embodiments, the one or more amino acids are present at a concentration between 10 mM and 200 mM. In some embodiments, the one or more amino acids are present at a concentration between 10 mM and 175 mM. In some embodiments, the one or more amino acids are present at a concentration between 10 mM and 150 mM. In some embodiments, the one or more amino acids are present at a concentration between 10 mM and 125 mM. In some embodiments, the one or more amino acids are present at a concentration between 10 mM and 100 mM. In some embodiments, the one or more amino acids are present at a concentration between 10 mM and 75 mM. In some embodiments, the one or more amino acids are present at a concentration between 10 mM and 50 mM. In some embodiments, the one or more amino acids are present at a concentration between 10 mM and 25 mM. In some embodiments, the one or more amino acids are present at a concentration between 20 mM and 250 mM. In some embodiments, the one or more amino acids are present at a concentration between 25 mM and 250 mM. In some embodiments, the one or more amino acids are present at a concentration between 50 mM and 250 mM. In some embodiments, the one or more amino acids are present at a concentration between 75 mM and 250 mM. In some embodiments, the one or more amino acids are present at a concentration between 100 mM and 250 mM. In some embodiments, the one or more amino acids are present at a concentration between 125 mM and 250 mM. In some embodiments, the one or more amino acids are present at a concentration between 150 mM and 250 mM. In some embodiments, the one or more amino acids are present at a concentration between 175 mM and 250 mM. In some embodiments, the one or more amino acids are present at a concentration between 200 mM and 250 mM. In some embodiments, the one or more amino acids are present at a concentration between 5 mM and 35 mM, between 10 mM and 35 mM, or between 15 mM and 30 mM.

In some embodiments of the invention, a formulation comprises one or more amino acids selected from arginine, glutamic acid, glycine, histidine and combinations thereof. In some embodiments, the formulation comprises arginine. In some embodiments, the formulation comprises glutamic acid. In some embodiments, the formulation comprises arginine and glutamic acid. In some embodiments, the formulation comprises histidine. In some embodiments, the formulation comprises glycine.

In some embodiments, a formulation comprising arginine comprises L-arginine or D-arginine. In some embodiments, a formulation comprising arginine comprises L-arginine hydrochloride or D-arginine hydrochloride. In some embodiments, the formulation comprises L-arginine. In some embodiments, the formulation comprises L-arginine hydrochloride. In some embodiments, the formulation comprises arginine at a concentration ranging from 10 mM to 250 mM. In some embodiments, the formulation comprises arginine at a concentration ranging from 10 mM to 225 mM. In some embodiments, the formulation comprises arginine at a concentration ranging from 10 mM to 200 mM. In some embodiments, the formulation comprises arginine at a concentration ranging from 10 mM to 175 mM. In some embodiments, the formulation comprises arginine at a concentration ranging from 10 mM to 150 mM. In some embodiments, the formulation comprises arginine at a concentration ranging from 10 mM to 125 mM. In some embodiments, the formulation comprises arginine at a concentration ranging from 10 mM to 100 mM. In some embodiments, the formulation comprises arginine at a concentration ranging from 10 mM to 75 mM. In some embodiments, the formulation comprises arginine at a concentration ranging from 10 mM to 50 mM. In some embodiments, the formulation comprises arginine at a concentration ranging from 10 mM to 25 mM. In some embodiments, the formulation comprises arginine at a concentration ranging from 10 mM to 20 mM. In some embodiments, the formulation comprises arginine at a concentration ranging from 20 mM to 250 mM. In some embodiments, the formulation comprises arginine at a concentration ranging from 25 mM to 250 mM. In some embodiments, the formulation comprises arginine at a concentration ranging from 50 mM to 250 mM. In some embodiments, the formulation comprises arginine at a concentration ranging from 75 mM to 250 mM. In some embodiments, the formulation comprises arginine at a concentration ranging from 100 mM to 250 mM. In some embodiments, the formulation comprises arginine at a concentration ranging from 125 mM to 250 mM. In some embodiments, the formulation comprises arginine at a concentration ranging from 150 mM to 250 mM. In some embodiments, the formulation comprises arginine at a concentration ranging from 175 mM to 250 mM. In some embodiments, the formulation comprises arginine at a concentration ranging from 200 mM to 250 mM. In some embodiments, the formulation comprises arginine at a concentration ranging from 225 mM to 250 mM. In some embodiments, the formulation comprises arginine at a concentration ranging from 20 mM to 30 mM, or 15 mM to 35 mM. In some embodiments, the formulation comprises arginine at a concentration of 25 mM. In some embodiments, the formulation comprises arginine at a concentration of 50 mM. In some embodiments, the formulation comprises arginine at a concentration of 75 mM. In some embodiments, the formulation comprises arginine at a concentration of 100 mM. In some embodiments, the formulation comprises arginine at a concentration of 125 mM. In some embodiments, the formulation comprises arginine at a concentration of 150 mM.

In some embodiments, the formulation comprises glutamic acid at a concentration ranging from 10 mM to 250 mM. In some embodiments, the formulation comprises glutamic acid at a concentration ranging from 10 mM to 200 mM. In some embodiments, the formulation comprises glutamic acid at a concentration ranging from 10 mM to 150 mM. In some embodiments, the formulation comprises glutamic acid at a concentration ranging from 10 mM to 100 mM. In some embodiments, the formulation comprises glutamic acid at a concentration ranging from 10 mM to 75 mM. In some embodiments, the formulation comprises glutamic acid at a concentration ranging from 10 mM to 50 mM. In some embodiments, the formulation comprises glutamic acid at a concentration ranging from 10 mM to 25 mM. In some embodiments, the formulation comprises glutamic acid at a concentration ranging from 10 mM to 20 mM. In some embodiments, the formulation comprises glutamic acid at a concentration ranging from 20 mM to 250 mM. In some embodiments, the formulation comprises glutamic acid at a concentration ranging from 25 mM to 250 mM. In some embodiments, the formulation comprises glutamic acid at a concentration ranging from 50 mM to 250 mM. In some embodiments, the formulation comprises glutamic acid at a concentration ranging from 75 mM to 250 mM. In some embodiments, the formulation comprises glutamic acid at a concentration ranging from 100 mM to 250 mM. In some embodiments, the formulation comprises glutamic acid at a concentration ranging from 125 mM to 250 mM. In some embodiments, the formulation comprises glutamic acid at a concentration ranging from 150 mM to 250 mM. In some embodiments, the formulation comprises glutamic acid at a concentration ranging from 200 mM to 250 mM. In some embodiments, the formulation comprises glutamic acid at a concentration of 50 mM. In some embodiments, the formulation comprises glutamic acid at a concentration of 75 mM. In some embodiments, the formulation comprises glutamic acid at a concentration of 100 mM. In some embodiments, the formulation comprises glutamic acid at a concentration of 125 mM. In some embodiments, the formulation comprises glutamic acid at a concentration of 150 mM.

In some embodiments, the formulation comprises arginine and glutamic acid at a ratio of at least 10:1, 5:1, 4:1, 3:1, 2:1, or 1:1. In some embodiments, the formulation comprises arginine and glutamic acid at a ratio of greater than or equal to 1:1. In some embodiments, the formulation comprises arginine and glutamic acid at a ratio equal to 1:1. In some embodiments, the formulation comprises arginine and glutamic acid at a ratio equal to 2:1. In some embodiments, the formulation comprises arginine and glutamic acid at a ratio equal to 3:1. In some embodiments, the formulation comprises arginine and glutamic acid at a ratio equal to 4:1. In some embodiments, the formulation comprises glutamic acid and arginine at a ratio of at least 10:1, 5:1, 4:1, 3:1, 2:1, or 1:1.

In some embodiments, the formulation comprises L-histidine. In some embodiments, the formulation comprises histidine at a concentration ranging from 5 mM to 25 mM. In some embodiments, the formulation comprises histidine at a concentration ranging from 5 mM to 20 mM. In some embodiments, the formulation comprises histidine at a concentration ranging from 5 mM to 15 mM. In some embodiments, the formulation comprises histidine at a concentration ranging from 5 mM to 10 mM. In some embodiments, the formulation comprises histidine at a concentration ranging from 10 mM to 25 mM. In some embodiments, the formulation comprises histidine at a concentration ranging from 15 mM to 25 mM. In some embodiments, the formulation comprises histidine at a concentration ranging from 20 mM to 25 mM. In some embodiments, the formulation comprises histidine at a concentration ranging from 15 mM to 25 mM, or between 10 mM to 30 mM. In some embodiments, the formulation comprises histidine at a concentration of 10 mM. In some embodiments, the formulation comprises histidine at a concentration of 20 mM.

In some embodiments, the formulation comprises glycine at a concentration ranging from 100 mM to 250 mM. In some embodiments, the formulation comprises glycine at a concentration ranging from 100 mM to 200 mM. In some embodiments, the formulation comprises glycine at a concentration ranging from 100 mM to 150 mM. In some embodiments, the formulation comprises glycine at a concentration ranging from 150 mM to 250 mM. In some embodiments, the formulation comprises glycine at a concentration ranging from 200 mM to 250 mM. In some embodiments, the formulation comprises glycine at a concentration of 150 mM. In some embodiments, the formulation comprises glycine at a concentration of 200 mM.

Buffers

In some embodiments of the invention, a formulation comprises a buffer to control pH. Suitable buffers include, for example, acetate, citrate, histidine, phosphate, succinate, tris(hydroxymethyl)aminomethane ("Tris") and other organic acids. In some embodiments, the formulation comprises a buffer selected from citrate, histidine, phosphate and succinate. In some embodiments, the formulation comprises a buffer at a concentration ranging from 5 mM to 100 mM. In some embodiments, the formulation comprises a buffer at a concentration ranging from 5 mM to 75 mM. In some embodiments, the formulation comprises a buffer at a concentration ranging from 5 mM to 50 mM. In some embodiments, the formulation comprises a buffer at a concentration ranging from 5 mM to 40 mM. In some embodiments, the formulation comprises a buffer at a concentration ranging from 5 mM to 30 mM. In some embodiments, the formulation comprises a buffer at a concentration ranging from 5 mM to 20 mM. In some embodiments, the formulation comprises a buffer at a concentration ranging from 5 mM to 10 mM. In some embodiments, the formulation comprises a buffer at a concentration ranging from 10 mM to 100 mM. In some embodiments, the formulation comprises a buffer at a concentration ranging from 20 mM to 100 mM. In some embodiments, the formulation comprises a buffer at a concentration ranging from 30 mM to 100 mM. In some embodiments, the formulation comprises a buffer at a concentration ranging from 40 mM to 100 mM. In some embodiments, the formulation comprises a buffer at a concentration ranging from 50 mM to 100 mM. In some embodiments, the formulation comprises a buffer at a concentration ranging from 75 mM to 100 mM. In some embodiments, the formulation comprises a buffer at a concentration of 10 mM. In some embodiments, the formulation comprises a buffer at a concentration of 20 mM.

In some embodiments, the formulation comprises phosphate. In some embodiments, the formulation comprises phosphate at a concentration ranging from 5 mM to 50 mM. In some embodiments, the formulation comprises phosphate at a concentration ranging from 5 mM to 40 mM. In some embodiments, the formulation comprises phosphate at a concentration ranging from 5 mM to 30 mM. In some embodiments, the formulation comprises phosphate at a concentration ranging from 5 mM to 20 mM. In some embodiments, the formulation comprises phosphate at a concentration ranging from 5 mM to 10 mM. In some embodiments, the formulation comprises phosphate at a concentration ranging from 10 mM to 50 mM. In some embodiments, the formulation comprises phosphate at a concentration ranging from 20 mM to 50 mM. In some embodiments, the formulation comprises phosphate at a concentration ranging from 30 mM to 50 mM. In some embodiments, the formulation comprises phosphate at a concentration ranging from 40 mM to 50 mM. In some embodiments, the formulation comprises phosphate at a concentration of 10 mM. In some embodiments, the formulation comprises phosphate at a concentration of 20 mM.

In some embodiments, the formulation comprises citrate. In some embodiments, the formulation comprises citrate at a concentration ranging from 5 mM to 50 mM. In some embodiments, the formulation comprises citrate at a concentration ranging from 5 mM to 40 mM. In some embodiments, the formulation comprises citrate at a concentration ranging from 5 mM to 30 mM. In some embodiments, the formulation comprises citrate at a concentration ranging from 5 mM to 20 mM. In some embodiments, the formulation comprises citrate at a concentration ranging from 5 mM to 10 mM. In some embodiments, the formulation comprises citrate at a concentration ranging from 10 mM to 50 mM. In some embodiments, the formulation comprises citrate at a concentration ranging from 20 mM to 50 mM. In some embodiments, the formulation comprises citrate at a concentration ranging from 30 mM to 50 mM. In some embodiments, the formulation comprises citrate at a concentration ranging from 40 mM to 50 mM. In some embodiments, the formulation comprises citrate at a concentration of 20 mM.

In some embodiments, the formulation comprises succinate. In some embodiments, the formulation comprises succinate at a concentration ranging from 5 mM to 50 mM. In some embodiments, the formulation comprises succinate at a concentration ranging from 5 mM to 40 mM. In some embodiments, the formulation comprises succinate at a concentration ranging from 5 mM to 30 mM. In some embodiments, the formulation comprises succinate at a concentration ranging from 5 mM to 20 mM. In some embodiments, the formulation comprises succinate at a concentration ranging from 5 mM to 10 mM. In some embodiments, the formulation comprises succinate at a concentration ranging from 10 mM to 50 mM. In some embodiments, the formulation comprises succinate at a concentration ranging from 20 mM to 50 mM. In some embodiments, the formulation comprises succinate at a concentration ranging from 30 mM to 50 mM. In some embodiments, the formulation comprises succinate at a concentration ranging from 40 mM to 50 mM. In some embodiments, the formulation comprises succinate at a concentration of 20 mM.

Salts

In some embodiments of the invention, a formulation further comprises a salt. Suitable salts include, for example, sodium chloride, potassium chloride, sodium sulfate and magnesium chloride. In some embodiments, the formulation comprises a halide. In some embodiments, the halide comprises an alkali metal halide. In some embodiments, the salt is sodium chloride (NaCl). In some embodiments, the formulation comprises NaCl at a concentration ranging from 50 mM to 175 mM. In some embodiments, the formulation comprises NaCl at a concentration ranging from 50 mM to 150 mM. In some embodiments, the formulation comprises NaCl at a concentration ranging from 50 mM to 125 mM. In some embodiments, the formulation comprises NaCl at a concentration ranging from 50 mM to 100 mM. In some embodiments, the formulation comprises NaCl at a concentration ranging from 50 mM to 75 mM. In some embodiments, the formulation comprises NaCl at a concentration ranging from 75 mM to 175 mM. In some embodiments, the formulation comprises NaCl at a concentration ranging from 100 mM to 175 mM. In some embodiments, the formulation comprises NaCl at a concentration ranging from 125 mM to 175 mM. In some embodiments, the formulation comprises NaCl at a concentration ranging from 150 mM to 175 mM. In some embodiments, the formulation comprises NaCl at a concentration ranging from 120 mM to 130 mM, or between 125 mM to 135 mM. In some embodiments, the formulation comprises NaCl at a concentration of 75 mM. In some embodiments, the formulation comprises NaCl at a concentration of 125 mM. In some embodiments, the formulation comprises NaCl at a concentration of 150 mM. In one embodiment, the molar ratio of NaCl to arginine is approximately 5:1. In another embodiment, the molar ratio of NaCl to histidine is approximately 6:1.

Surfactants

In some embodiments of the invention, a formulation further comprises a surfactant. Exemplary surfactants include nonionic surfactants such as polysorbates (e.g., polysorbate 20, polysorbate 40, or polysorbate 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethylene glycol (PEG), polypropylene glycol, and copolymers of ethylene and propylene glycol (e.g., Pluronics, PF68, etc). Typically, the amount of surfactant added is such that it reduces aggregation of the antibody and minimizes the formation of particulates. For example, a surfactant may be present in a formulation at a concentration from about 0.001-0.5% (e.g., about 0.075%). In particular, a surfactant may be present in a formulation at a concentration of approximately 0.005%, 0.01%, 0.02%, 0.05%, 0.1%, etc. In some embodiments, a surfactant may be present in a formulation at a concentration of approximately 0.03%. In some embodiments, a surfactant may be present in a formulation at a concentration of approximately 0.07%. In some embodiments, a surfactant may be present in a formulation at a concentration of approximately 0.1%. In some embodiments, a formulation comprises polysorbate 80 (PS80) at a concentration of approximately 0.03%. In some embodiments, a formulation comprises polysorbate 80 (PS80) at a concentration of approximately 0.07%. In some embodiments, a formulation comprises polysorbate 80 (PS80) at a concentration of approximately 0.05%. In some embodiments, a formulation comprises polysorbate 80 (PS80) at a concentration of approximately 0.1%. Alternatively, or in addition, the surfactant may be added to a lyophilized formulation, pre-lyophilized formulation and/or a reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium. In some embodiments of the invention, a formulation comprises an excipient, wherein the excipient is a polyol. Suitable polyol excipients include, for example, mannitol and sorbitol. In some embodiments, the formulation comprises mannitol at a concentration ranging from 50 mM to 200 mM. In some embodiments, the formulation comprises mannitol at a concentration ranging from 60 mM to 170 mM. In some embodiments, the formulation comprises sorbitol at a concentration ranging from 2-8% by weight. In some embodiments, the formulation comprises sorbitol at a concentration ranging from 2.5-5% by weight.

pH and Isoelectric Point (pI)

In some embodiments of the invention, formulations were created with different pH levels in order to determine the effect of pH on formulation properties such as viscosity and stability (e.g., monomer purity, increase in high molecular weight (HMW) species, loss of main charge variant and charge distribution). Typically, when creating formulations, pH values close to the isoelectric point (pI) (the pH at which the effective charge on a protein is zero) are avoided because solubility is usually minimal at or near the pI value. Virtually all proteins display a V- or U-shaped plot of solubility vs. pH, with the bottom being at the pI value. This behavior is due to minimal electrostatic repulsion being present at the pI, thereby reducing the colloidal stability of the protein, which leads to decreased solubility, increased viscosity, and elevated likelihood of aggregation. Generally, as the pH of a formulation either increases or decreases, the overall charge on the protein increases, leading to increased electrostatic repulsion and improved colloidal stability. Remarkably, when different formulations comprising an anti-OSMR antibody were tested, it was determined that pH values not only close to the pI, but actually overlapping it (e.g., pH of 6.0 to 7.5 and pI of 7.0-8.0), were effective at maintaining stability, while still allowing antibody concentrations of ≥200 mg/mL to be achieved. Additionally, formulations under these pH conditions displayed viscosities that were surprisingly low for high concentration formulations of a monoclonal antibody. This was not expected, as one of skill in the art would have predicted lower solubility and/or higher viscosity under these conditions.

In some embodiments, pH values in the range of 6.0-7.6 keep the viscosity of the formulation at levels that allow subcutaneous administration (e.g., less than 30 mPa*s) when the antibody concentration is, for example, in the range of approximately 150 mg/mL and approximately 250 mg/mL. In some embodiments, an increase in HMW species of an anti-OSMR antibody occurs in formulations at pH≤6.0. In some embodiments, loss of the main charge variant peak of an anti-OSMR antibody in the formulation is correlated with the pH of the formulation. In some embodiments, higher pH formulations have a greater loss of the main charge variant peak after weeks in storage, with the loss mainly due to formation of acidic species. In certain embodiments, an increase in HMW species or loss of the charge variant peak of the anti-OSMR antibody in storage is determined at 2, 4, 6 or 8 weeks in storage and at approximately 5° C., 25° C. or 40° C. In some embodiments, a formulation according to the present invention has a pH ranging from approximately 6.0-7.6. In some embodiments, a formulation according to the present invention has a pH ranging from approximately 6.6-7.2. In some embodiments, a formulation according to the present invention has a pH selected from 6.6, 6.8, 7.0, 7.2 and 7.6.

In some embodiments, a formulation according to the present invention comprises an anti-OSMR antibody that has a pI ranging from approximately 6.5-8.5. In some embodiments, a formulation according to the present invention comprises an anti-OSMR antibody that has a pI ranging from approximately 7.2 to 8.0. In some embodiments, a formulation according to the present invention comprises an anti-OSMR antibody that has a pI ranging from approximately 6.5-8.5 and has a pH that overlaps with pI of the anti-OSMR antibody. In some embodiments, a formulation according to the present invention has an anti-OSMR antibody concentration of at least 150 mg/mL (e.g., between about 150 mg/mL and about 175 mg/mL, between about 175 mg/mL and 200 mg/mL, between about 200 mg/mL and 225 mg/mL, and between about 225 mg/mL and 250 mg/mL), pH ranging from 6.0 to 7.6, and a pI ranging from 7 to 8. In one embodiment, the anti-OSMR antibody is present at a concentration of between about 150 mg/mL and 210 mg/ml, having a pH ranging from approximately 6.6 to 6.8 and a pI ranging from approximately 7.2 to 8.0.

In some embodiments, the formulation is an isoltonic solution. In some embodiments the isotonic formulation comprises an osmolarity ranging between 250 and 350 mOsm. In some embodiments, the of the osmolarity formulation ranges between 260-330 mOsm. In some embodiments the osmolarity of the formulation ranges anywhere between 250, 260, 270, 280, 290, 300, 310, 320, 330, 340 or 350 mOsm. In some embodiments, the osmolarity of the formulation ranges between 270-300 mOsm.

Viscosity

In some embodiments of the invention, a formulation is a liquid. In some embodiments of the invention, formulations were optimized in order to reduce viscosity, while maintaining high antibody concentration. Using a constant rate of 0.1 mL/minute, the force required to either aspirate (syringeability) or expel (injectability) the material from/into the syringe can be recorded. In some embodiments, lower viscosity allows for increased injectability of a formulation or effective sample transfer and preparation during manufacturing. In some embodiments, a formulation has a viscosity, as measured by microfluidic rheometer, ranging from 1 mPa*s to 30 mPa*s. In some embodiments, a formulation has a viscosity of less than 25 mPa*s, as measured by microfluidic rheometer. In some embodiments, a formulation has a viscosity of less than 20 mPa*s, as measured by microfluidic rheometer. In some embodiments, a formulation has a viscosity of less than 15 mPa*s, as measured by microfluidic rheometer. In some embodiments, a formulation has a viscosity, as measured by a microfluidic rheometer, between approximately 1 and 30 mPa*s. In some embodiments, a formulation has a viscosity, as measured by a microfluidic rheometer, between approximately 2 and 30 mPa*s. In some embodiments, a formulation has a viscosity, as measured by a microfluidic rheometer, between approximately 4 and 30 mPa*s. In some embodiments, a formulation has a viscosity, as measured by a microfluidic rheometer, between approximately 6 and 30 mPa*s. In some embodiments, a formulation has a viscosity, as measured by a microfluidic rheometer, between approximately 8 and 30 mPa*s. In some embodiments, a formulation has a viscosity, as measured by a microfluidic rheometer, between approximately 10 and 30 mPa*s. In some embodiments, a formulation has a viscosity, as measured by a microfluidic rheometer, between approximately 12 and 30 mPa*s. In some embodiments, a formulation has a viscosity, as measured by a microfluidic rheometer, between approximately 14 and 30 mPa*s. In some embodiments, a formulation has a viscosity, as measured by a microfluidic rheometer, between approximately 16 and 30 mPa*s. In some embodiments, a formulation has a viscosity, as measured by a microfluidic rheometer, between approximately 18 and 30 mPa*s. In some embodiments, a formulation has a viscosity, as measured by a microfluidic rheometer, between approximately 20 and 30 mPa*s. In some embodiments, a formulation has a viscosity, as measured by a microfluidic rheometer, between approximately 22 and 30 mPa*s. In some embodiments, a formulation has a viscosity, as measured by a microfluidic rheometer, between approximately 24 and 30 mPa*s. In some embodiments, a formulation has a viscosity, as measured by a microfluidic rheometer, between approximately 26 and 30 mPa*s. In some embodiments, a formulation has a viscosity, as measured by a microfluidic rheometer, between approximately 28 and 30 mPa*s. In some embodiments, a formulation has a shear rate of less than $1000$ $s^{-1}$ at 25° C.

In some embodiments, the formulation has the viscosity such that it is injectable via a regular syringe and needle combination, the needle having a nominal internal diameter of about 0.1 to about 0.6 mm. In some embodiments, the formulation is injectable by a needle having an internal diameter of about 0.1, or about 0.2 or about 0.3, or about 0.4 or about 0.5, or about 0.6 mm. In some embodiments, the formulation has the viscosity such that it is injectable via a regular syringe and needle combination, the needle having a nominal internal diameter of about 0.18 to about 0.3 mm. In some embodiments, the formulation has a viscosity such that it is injectable using a needle having an internal diameter between about 0.184 mm to about 0.260 mm diameter. In some embodiments, the formulation has the viscosity such that it is injectable via a regular syringe and needle combination, the needle having a nominal internal diameter of about 0.184 to 0.210 mm. In some embodiments, the formulation has a viscosity such that it is injectable using 27G ½" gauge needle and a 2 ml syringe. In some embodiments, the pound force required to inject the formulation at a constant rate of 0.1 mL/second is less than about 8.0 pound force. In some embodiments, the pound force required to inject the formulation at a constant rate of 0.1 mL/second is less than about 8 pound force, less than about 7.5 pound force, or less than about 6.9 pound force, less than about 6.8 pound force, less than about 6.7 pound force, less than about 6.7 pound force, less than about 6.6 pound force or less than about 6.5 pound force.

Stability

In some embodiments of the invention, formulations were optimized in order to increase stability. The stability of an antibody formulation can be quantified in several ways. In some embodiments, stability of an antibody formulation is characterized by the amount of HMW species of an anti-OSMR antibody or the rate of increase of the amount of HMW species of an anti-OSMR antibody. In certain embodiments, the rate of increase of HMW species is determined at 2, 4, 6 or 8 weeks in storage and at approximately 5° C., 25° C. or 40° C. In some embodiments, stability of an antibody formulation is characterized by charge distribution, e.g., a change in the amount of the charge variant peaks of the antibody. In some embodiments, stability of an antibody formulation is characterized by dynamic light scattering, analytical ultracentrifugation (AUC), field flow fractionation (FFF), isoelectric focusing and ion exchange chromatography (IEX). In some embodiments, stability of an antibody formulation is characterized by partial dissociation as measured by sodium-dodecyl sulfate capillary electrophoresis (CE-SDS) and/or sodium-dodecyl sulfate polyacrylamide gel electrophoresis (SDS-PAGE).

The stability of an anti-OSMR antibody, and the capability of the formulation to maintain stability of the anti-OSMR antibody, may be assessed over extended periods of time (e.g., weeks or months). In the context of a formulation, a stable formulation is one in which the antibody therein essentially retains its physical and/or chemical integrity and biological activity upon storage and during processes such as freeze/thaw, mechanical mixing and lyophilization. Antibody stability can be measured by formation of high molecular weight (HMW) aggregates, shift of charge profiles, and change in particle size.

Stability of an antibody may be assessed relative to the biological activity or physiochemical integrity of the antibody over extended periods of time. For example, stability at a given time point may be compared against stability at an earlier time point (e.g., upon formulation day 0), against unformulated antibody, or against a differently formulated antibody and the results of this comparison expressed as a percentage. Preferably, the antibody formulations of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the antibody's biological activity, physiochemical integrity, and/or particle size over an extended period of time (e.g., as measured over at least about 1, 2, 3, 4, 5, 6, 7, 8, 9, 10, 11, 12, 18, 24, or 36 months, at room temperature or under accelerated storage conditions). In some embodiments, the percent values indicating protein levels as disclosed herein or throughout the specification, are expressed relative to the total protein in the formulation. In some embodiments, the relative values of any particular species of the product, as disclosed herein or throughout the specification, such as the monomeric IgG form or species, or the high molecular weight (HMW) form, or the aggregated forms, are expressed in relation to the respective values of the total product. In some embodiments, the percent values of any particular species of the antibody are expressed relative to the total amount of all antibody-related species in the formulation. In some embodiments, less than 5%, 4%, 3%, 2%, 1%, or 0.5% of an anti-OSMR antibody exists as HMW species in a formulation. In some embodiments, the amount of HMW species in a formulation increases less than 5%, 4%, 3%, 2%, 1%, or 0.5% upon storage at 25° C. for more than 2 weeks. In some embodiments, upon storage at 25° C. for 4 weeks, the amount of HMW species in the formulation increases approximately between 0.3% to 0.7%, approximately between 0.3% to 0.6%, or approximately between 0.3% to 0.5%. In some embodiments, at least 90%, 92%, 94%, 95%, 96%, 97%, 98%, or 99% of an anti-OSMR antibody exists as monomer in a stable formulation. In some embodiments, the amount of monomer decreases less than 10%, 8%, 6%, 5%, 4%, 3%, 2%, 1%, or 0.5% upon storage at 25° C. for more than 2 weeks, for example, for 4 weeks.

Delivery

In some embodiments of the invention, formulations comprise high anti-OSMR antibody concentrations suitable for subcutaneous, intradermal, intramuscular and/or intra-articular delivery. In some embodiments, a formulation comprises an anti-OSMR antibody at a concentration of at least approximately 50 mg/mL. In some embodiments, a formulation comprises an anti-OSMR antibody at a concentration of at least approximately 75 mg/mL. In some embodiments, a formulation comprises an anti-OSMR antibody at a concentration of at least approximately 100 mg/mL. In some embodiments, a formulation comprises an anti-OSMR antibody at a concentration of at least approximately 125 mg/mL. In some embodiments, a formulation comprises an anti-OSMR antibody at a concentration of at least approximately 150 mg/mL. In some embodiments, a formulation comprises an anti-OSMR antibody at a concentration of at least approximately 175 mg/mL. In some embodiments, a formulation comprises an anti-OSMR antibody at a concentration of at least approximately 200 mg/mL. In some embodiments, a formulation comprises an anti-OSMR antibody at a concentration of at least approximately 225 mg/mL. In some embodiments, a formulation comprises an anti-OSMR antibody at a concentration of at least approximately 250 mg/mL.

In some embodiments, the volume of an anti-OSMR antibody formulation delivered by subcutaneous, intradermal, intramuscular and/or intra-articular injection is 10 mL or less. In some embodiments, the volume of an anti-OSMR antibody formulation delivered by subcutaneous, intradermal, intramuscular and/or intra-articular injection is 5 mL or less. In some embodiments, the volume of an anti-OSMR antibody formulation delivered by subcutaneous, intradermal, intramuscular and/or intra-articular injection is 4 mL or less. In some embodiments, the volume of an anti-OSMR antibody formulation delivered by subcutaneous, intradermal, intramuscular and/or intra-articular injection is 3 mL or less. In some embodiments, the volume of an anti-OSMR antibody formulation delivered by subcutaneous, intradermal, intramuscular and/or intra-articular injection is 2 mL or less. In some embodiments, the volume of an anti-OSMR antibody formulation delivered by subcutaneous, intradermal, intramuscular and/or intra-articular injection is 1 mL or less. In some embodiments, the volume of an anti-OSMR antibody formulation delivered by subcutaneous, intradermal, intramuscular and/or intra-articular injection is 0.5 mL or less.

In some embodiments, the volume of an anti-OSMR antibody formulation delivered by subcutaneous injection is 10 mL or less. In some embodiments, the volume of an anti-OSMR antibody formulation delivered by subcutaneous injection is 5 mL or less. In some embodiments, the volume of an anti-OSMR antibody formulation delivered by subcutaneous injection is 4 mL or less. In some embodiments, the volume of an anti-OSMR antibody formulation delivered by subcutaneous injection is 3 mL or less. In some embodiments, the volume of an anti-OSMR antibody formulation delivered by subcutaneous injection is 2 mL or less. In some embodiments, the volume of an anti-OSMR antibody formulation delivered by subcutaneous injection is 1 mL or less. In some embodiments, the volume of an anti-OSMR antibody formulation delivered by subcutaneous injection is 0.5 mL or less. In some embodiments the volume of an anti-OSMR antibody formulation delivered by subcutaneous injection is 3 mL. In some embodiments the volume the volume of an anti-OSMR antibody formulation delivered by subcutaneous injection is 2 mL. In some embodiments the volume the volume of an anti-OSMR antibody formulation delivered by subcutaneous injection is 1 mL. In some embodiments the volume of an anti-OSMR antibody formulation delivered by subcutaneous injection is 0.5 mL.

In some embodiments, subcutaneous injection of the anti-OSMR antibody formulation can be performed in the upper arm, the anterior surface of the thigh, the lower portion of the abdomen, the upper back or the upper area of the buttock. In some embodiments, the site of injection is rotated.

In some embodiments, formulations of the present invention may be designed for delivery by any suitable route, including but not limited to, subcutaneous, intradermal, intra-articular, oral, rectal, and vaginal, and by parenteral routes, including intravenous and intra-arterial injection, and intramuscular injection.

Kits

The present invention further provides kits or other articles of manufacture which contain the formulation of the present invention and provides instructions for its reconstitution (if lyophilized) and/or use. Kits or other articles of manufacture may include a container, a needle, and any other articles, devices or equipment useful in subcutaneous administration. Suitable containers include, for example, bottles, vials, syringes (e.g., pre-filled syringes), subcutaneous pumps, ampules, cartridges, reservoirs, or lyo-jects. The container may be formed from a variety of materials such as glass or plastic. In some embodiments, a container is a prefilled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to antibody concentrations as described above. The label may further indicate that the formulation is useful or intended for, for example, subcutaneous administration. In some embodiments, a container may contain a single dose of a stable formulation containing a therapeutic antibody (e.g., an anti-OSMR antibody). In various embodiments, a single dose of the stable formulation is present in a volume of less than about 10 mL, 5.0 mL, 4.0 mL, 3.5 mL, 3.0 mL, 2.5 mL, 2.0 mL, 1.5 mL, 1.0 mL, or 0.5 mL.

Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final antibody concentration in the reconstituted formulation will generally be at least 150 mg/mL (e.g., at least 160 mg/mL, at least 170 mg/mL, at least 180 mg/mL, at least 190 mg/mL, at least 200 mg/mL). Kits or other articles of manufacture may further include other materials desirable from a commercial and user standpoint, including other buffers, diluents, preservatives, filters, needles, syringes, and package inserts with instructions for use.

Treatment of Diseases and Disorders Associated with OSMR

Anti-OSMR antibody formulations and compositions of the present invention are used to treat an autoimmune disorder, inflammatory disorder, or a disorder associated with extracellular matrix deposition or remodeling. In treating these disorders, the anti-OSMR antibody may target OSMR-expressing cells of the immune system for destruction and/or may block the interaction of OSMR with OSM and/or IL-31. Diseases or disorders that are associated with OSMR-mediated signaling are particularly amenable to treatment with the anti-OSMR antibodies of the present invention. One such disorder is pruritus. Other diseases and disorders that are associated with OSMR-mediated signaling and are particularly amenable to treatment with the anti-OSMR antibodies of the present invention include, but are not limited to, inflammation, pain, prurigo nodularis, dermatitis, atopic dermatitis, asthma, autoimmune disease, paraneoplastic autoimmune diseases, cartilage inflammation, fibrosis (including, but not limited to, pulmonary fibrosis and skin fibrosis), fibrotic disease, chronic obstructive pulmonary disease (COPD), interstitial pneumonitis, abnormal collagen deposition, systemic cutaneous amyloidosis, primary cutaneous amyloidosis, Behcet's disease, nasal polyposis, liver cirrhosis, cartilage degradation, bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, scleroderma-associated interstitial lung disease, vasculitis, myolitis, polymyolitis, dermatomyolitis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophagitis, eosinophilic bronchitis, bronchitis, Guillain-Barre disease, Type I diabetes mellitus, thyroiditis (e.g., Graves' disease), Addison's disease, Reynaud's phenomenon, autoimmune hepatitis, GVHD, transplantation rejection, kidney damage, cardiovascular disease, infection, sepsis, HIV infection, trauma, kidney allograft nephropathy, IgA nephropathy, diabetic nephropathy, diabetic retinopathy, macular degeneration, biliary atresia, congestive heart failure, atherosclerosis, restenosis, radiation-induced fibrosis, chemotherapy-induced fibrosis, burns, surgical trauma, glomerulosclerosis, and the like.

Formulations, compositions and methods of the present invention may be used to effectively treat individuals suffering from or susceptible to pruritus. The terms, "treat" or "treatment," as used herein, refers to amelioration of one or more symptoms associated with pruritus, prevention or delay of the onset of one or more symptoms of pruritus, and/or lessening of the severity or frequency of one or more symptoms of pruritus.

EXAMPLES

While certain formulations, compositions and methods of the present invention have been described with specificity in accordance with certain embodiments, the following examples serve only to illustrate the compounds of the invention and are not intended to limit the same.

Example 1: Characterization of Anti-OSMR Antibody

The exemplary anti-OSMR antibodies described herein are fully human monoclonal antibodies that specifically inhibit IL-31 and oncostatin M (OSM)-induced activation of the IL-31 receptor and type II OSM receptor, respectively, through binding to OSMRβ, the subunit common to both receptors. The antibody comprises two light chains and two heavy chains. The light chain contains a lambda constant region. The constant regions of the heavy chain contain the CH1, hinge, and CH2 domains of a human immunoglobulin IgG4 antibody fused to the CH3 domain of a human IgG1 antibody. Additionally, the heavy chain of the anti-OSMR antibody contains a S228P modification to improve stability and a N297Q modification to remove an N-linked glycosylation site.

An exemplary anti-OSMR antibody comprises a heavy chain amino acid sequence of SEQ ID NO: 1 and a light chain amino acid sequence of SEQ ID NO: 2. The exemplary anti-OSMR antibody also comprises a heavy chain variable domain amino acid sequence of SEQ ID NO: 3 and a light chain variable domain amino acid sequence of SEQ ID NO: 4. The exemplary anti-OSMR antibody also comprises a heavy chain variable domain CDR1 (HCDR1) of SEQ ID NO: 5, a heavy chain variable domain CDR2 (HCDR2) of SEQ ID NO: 6, a heavy chain variable domain CDR3 (HCDR3) of SEQ ID NO: 7, a light chain variable domain CDR1 (LCDR1) of SEQ ID NO: 8, a light chain variable domain CDR2 (LCDR2) of SEQ ID NO: 9, and a light chain variable domain CDR3 (LCDR3) of SEQ ID NO: 10. The exemplary anti-OSMR antibody also comprises a heavy chain signal peptide amino acid sequence of SEQ ID NO: 11, a heavy chain amino acid sequence comprising IgG4 CH1, hinge, and CH2 domains of SEQ ID NO: 12, a heavy chain IgG1 CH3 domain amino acid sequence of SEQ ID NO: 13 and a light chain IgG lambda constant domain amino acid sequence of SEQ ID NO: 14.

Charge heterogeneity was assessed by imaged capillary isoelectric focusing (icIEF). The protein isoforms were separated based on pI and the elution profile was monitored by UV absorbance at 280 nm.

Example 2: Formulation Design and Preparation

Four rounds of formulations were created in order to test the effect of protein concentration, buffer species, pH and inclusion of excipients on variables such as viscosity and stability. Table 1, Table 2, Table 3 and Table 4 below detail the formulation designs for the four rounds of formulations.

TABLE 1

Round 1 Formulation Design

| Sample | Target protein (mg/ml) | Target pH | Citrate (mM) | His (mM) | Phosphate (mM) | Succinate (mM) | Arg (mM) | NaCl (mM) | Sorb. (wt %) | PS 80 (%) |
|---|---|---|---|---|---|---|---|---|---|---|
| F01 | 100 | 6.6 | 20 | 0 | 0 | 0 | 150 | 0 | 0 | 0.075 |
| F02 | 125 | 6.6 | 20 | 0 | 0 | 0 | 150 | 0 | 0 | 0.075 |
| F03 | 150 | 6.6 | 20 | 0 | 0 | 0 | 150 | 0 | 0 | 0.075 |
| F04 | 150 | 6 | 0 | 0 | 0 | 20 | 0 | 75 | 2.5 | 0.075 |
| F05 | 50 | 6.6 | 0 | 20 | 0 | 0 | 0 | 150 | 0 | 0.075 |
| F06 | 100 | 7.6 | 0 | 20 | 0 | 0 | 0 | 0 | 5 | 0.075 |
| F07 | 100 | 7.2 | 0 | 0 | 20 | 0 | 0 | 0 | 5 | 0.075 |
| F08 | 150 | 7.2 | 0 | 20 | 0 | 0 | 0 | 0 | 5 | 0.075 |
| F09 | 175 | 7.6 | 0 | 20 | 0 | 0 | 75 | 75 | 0 | 0.075 |
| F10 | 125 | 7.2 | 0 | 20 | 0 | 0 | 25 | 0 | 5 | 0.075 |
| F11 | 50 | 6.6 | 0 | 0 | 20 | 0 | 0 | 150 | 0 | 0.075 |
| F12 | 100 | 6 | 0 | 0 | 20 | 0 | 0 | 0 | 5 | 0.075 |
| F13 | 50 | 7.6 | 0 | 0 | 20 | 0 | 0 | 150 | 0 | 0.075 |
| F14 | 150 | 6.6 | 0 | 0 | 0 | 20 | 25 | 0 | 5 | 0.075 |
| F15 | 125 | 5.4 | 20 | 0 | 0 | 0 | 0 | 0 | 5 | 0.075 |
| F16 | 100 | 5.4 | 0 | 0 | 0 | 20 | 0 | 75 | 2.5 | 0.075 |

TABLE 2

Round 2 Formulation Design

| Sample | Target protein (mg/ml) | pH | citrate (mM) | His (mM) | Phosphate (mM) | succinate (mM) | Arg (mM) | Glu (mM) | Gly (mM) | NaCl (mM) | mannitol (mM) | PS 80 (%) |
|---|---|---|---|---|---|---|---|---|---|---|---|---|
| F01 | 200 | 6.57 | 20 | 0 | 0 | 0 | 150 | 0 | 0 | 0 | 0 | 0.1 |
| F02 | 200 | 6.75 | 0 | 0 | 0 | 0 | 150 | 0 | 0 | 0 | 0 | 0.1 |

TABLE 2-continued

Round 2 Formulation Design

| Sample | Target protein (mg/ml) | pH | citrate (mM) | His (mM) | Phosphate (mM) | succinate (mM) | Arg (mM) | Glu (mM) | Gly (mM) | NaCl (mM) | mannitol (mM) | PS 80 (%) |
|---|---|---|---|---|---|---|---|---|---|---|---|---|
| F03 | 200 | 6.58 | 0 | 0 | 10 | 0 | 50 | 0 | 0 | 75 | 0 | 0.1 |
| F04 | 200 | 6.74 | 0 | 0 | 0 | 0 | 25 | 0 | 200 | 0 | 0 | 0.1 |
| F05 | 200 | 6.66 | 0 | 20 | 0 | 0 | 0 | 150 | 0 | 0 | 0 | 0.1 |
| F06 | 200 | 6.56 | 0 | 0 | 0 | 20 | 150 | 0 | 0 | 0 | 0 | 0.1 |
| F07 | 200 | 6.98 | 0 | 20 | 0 | 0 | 50 | 0 | 150 | 0 | 0 | 0.1 |
| F08 | 200 | 7.12 | 0 | 0 | 20 | 0 | 50 | 0 | 0 | 0 | 170 | 0.1 |
| F09 | 200 | 6.84 | 0 | 0 | 0 | 20 | 25 | 0 | 0 | 125 | 0 | 0.1 |
| F10 | 200 | 6.59 | 0 | 0 | 0 | 0 | 25 | 0 | 0 | 125 | 0 | 0.1 |
| F11 | 200 | 6.68 | 0 | 10 | 0 | 0 | 50 | 50 | 0 | 0 | 60 | 0.1 |
| F12 | 200 | 6.95 | 0 | 10 | 0 | 0 | 50 | 50 | 0 | 0 | 60 | 0.1 |
| F13 | 200 | 7.08 | 0 | 10 | 0 | 0 | 50 | 50 | 0 | 0 | 60 | 0.1 |
| F14 | 200 | 6.97 | 0 | 0 | 10 | 0 | 100 | 100 | 0 | 0 | 0 | 0.1 |
| F15 | 200 | 6.66 | 0 | 10 | 0 | 0 | 100 | 100 | 0 | 0 | 0 | 0.1 |
| F16 | 200 | 6.60 | 0 | 10 | 0 | 0 | 0 | 0 | 0 | 75 | 120 | 0.1 |
| F17 | 200 | 6.57 | 0 | 10 | 0 | 0 | 0 | 0 | 0 | 150 | 0 | 0.1 |
| F18 | 200 | 6.58 | 0 | 10 | 0 | 0 | 150 | 0 | 0 | 0 | 0 | 0.1 |

TABLE 3

Round 3 Formulation Design

| Sample | Target pH | citrate (mM) | His (mM) | Phosphate (mM) | succinate (mM) | Arg (mM) | Glu (mM) | Gly (mM) | NaCl (mM) | mannitol (mM) | PS 80 (%) |
|---|---|---|---|---|---|---|---|---|---|---|---|
| F01 | 6.6 | 0 | 20 | 0 | 0 | 25 | 0 | 0 | 125 | 0 | 0.075 |
| F02 | 6.6 | 0 | 20 | 0 | 0 | 150 | 0 | 0 | 0 | 0 | 0.075 |
| F03 | 6.6 | 0 | 20 | 0 | 0 | 75 | 0 | 0 | 75 | 0 | 0.075 |

TABLE 4

Round 4 Formulation Design

| Sample | Target Protein (mg/ml) | Target pH | citrate (mM) | His (mM) | Phosphate (mM) | succinate (mM) | Arg (mM) | Glu (mM) | Gly (mM) | NaCl (mM) | mannitol (mM) | PS 80 (%) |
|---|---|---|---|---|---|---|---|---|---|---|---|---|
| F01 | 200 | 6.6 | 0 | 20 | 0 | 0 | 25 | 0 | 0 | 125 | 0 | variable |
| F02 | 200 | 6.6 | 0 | 20 | 0 | 0 | 150 | 0 | 0 | 0 | 0 | variable |

Formulations for Rounds 1, 2 and 3 were prepared by dialyzing the bulk drug substance (BDS) against the formulation placebo (buffer and tonicity modifiers) with Slide-A-Lyzer Mini Dialysis devices (20 kD MWCO, 2 mL capacity). The following dialysis procedure was utilized: 4 hours against milliQ water, 2 hours at room temperature against placebo with orbital shaking at 300 rpm (3 mm-orbital radius shaker) followed by an additional 2 exchanges against placebo and another 4 hours at room temperature (2 hours per exchange, 300 rpm orbital shaking), and finally another buffer exchange and dialysis at 2-8° C. (orbital shaking, 300 rpm) for an additional 17-24 hours. If needed, polysorbate 80 (PS80) was spiked into a given formulation from a 10% (w/v) stock solution prepared in milliQ water. Formulations for Round 4 were prepared in a similar manner, with the exception that dialysis was conducted with a Slide-A-Lyzer Dialysis Cassette to reduce the shear experienced by the PS80-free protein during dialysis. All samples were concentrated to the target concentration using centrifugal spin concentrators.

The drug substance comprising an API concentration of 209 mg/mL in a formulation buffer comprising 20 mM L-histidine, 25 mM L-arginine hydrochloride, 125 mM sodium chloride, 0.05% (w/v) polysorbate 80, pH 6.6-6.8 was subjected to stress, stability, freeze thaw and drug production stress studies. For in-use compatibility studies, the drug substance was diluted to 180 mg/mL by formulation buffer. A placebo control is 20 mM L-Histidine, 25 mM L-Arginine-HCl, 125 mM NaCl, 0.05% (w/v) PS80, pH 6.6.

Sub-ambient differential scanning calorimetry (DSC) analysis determined the glass transition temperature (Tg') of the formulation at both 208.8 mg/mL and 180 mg/mL, to be ~−34.3° C. Density measurements taken by densitometer at 25° C. on the formulation at 180 mg/mL, as well as placebo, were 1.0588 g/cm$^3$ and 1.0050 g/cm$^3$, respectively. All samples were free of visible particulates. Over the course of 24 hours, no change in appearance was detected in comparison to time zero.

For the preparation of individual stability samples, each formulation (bulk material) was sterile filtered using a Millipore Millex-GV syringe filter (0.22 μm). After filtration, 0.5 mL was aliquotted into 1 mL glass vials, stoppered (13 mm rubber stopper), and sealed with crimped aluminum caps. Sterile filtering and aliquotting was conducted in a biosafety cabinet using materials (i.e., vials, stoppers, etc.) that had been previously sterilized.

Injectability was assessed by Instron Mechanical Tester, examined the pound-force required to expel the drug product at a constant rate of 0.1-mL/min, using different needle gauges and lengths, as well as sample temperatures of 18° C. and 25°. Results show that the drug product at 180 mg/mL, at 25° C., expelled via a 27G ½" needle required 6.5 pound-force.

Example 3: Viscosity

The viscosity of samples from Round 1 and Round 2 was measured for non-stressed material (nominally t0). Viscosity was measured using a Rheosense m-VROC rheometer at a shear rate of 1000 s$^{-1}$ and a temperature of 25° C. A 100 μL Hamilton gas-tight syringe filled with 100 μL (nominally) of a given formulation was used to perform a measurement. Generally, 4 measurements per formulation were collected with the last 2 being averaged and reported as the formulation viscosity. The viscosity results from Round 1 are shown below in Table 5, the viscosity results from Round 2 are shown below in Table 6, and the viscosity results from Round 3 are shown below in Table 7. A graph illustrating the effect of protein concentration on viscosity from two Round 3 formulations is shown in FIG. 1.

Concentration of the anti-OSMR antibody was determined using UV-absorbance spectroscopy. Briefly, absorbance of diluted the anti-OSMR antibody was determined at 280 nm in a 1 cm path-length UV transparent cuvette and corrected for scattering by subtracting out the absorbance of the sample at 320 nm. Absorbance was determined against a blank without protein and converted to protein content utilizing Beer's law ($\varepsilon_{280,\ 1\ cm}$=1.62 ml/mg*cm). Since samples were diluted to make the measurement, it was necessary to multiply this concentration by the dilution factor (gravimetric) to obtain actual concentration.

TABLE 5

Round 1 Viscosity

| Sample | Actual pH | Actual Conc. (mg/mL) | Visc. (mPa * s) |
| --- | --- | --- | --- |
| F01 | 6.60 | 96.0 | 2.3 |
| F02 | 6.59 | 126.0 | 3.2 |
| F03 | 6.57 | 144.6 | 5.3 |
| F04 | 6.01 | 145.0 | 6.3 |
| F05 | 6.57 | 49.4 | 1.3 |
| F06 | 6.89 | 98.8 | 3.3 |
| F07 | 7.17 | 100.7 | 3.1 |
| F08 | 6.60 | 147.4 | 8.2 |
| F09 | 7.50 | 166.7 | 8.3 |
| F10 | 7.19 | 126.5 | 4.5 |
| F11 | 6.54 | 51.2 | 1.4 |
| F12 | 6.09 | 95.9 | 3.1 |
| F13 | 7.47 | 49.6 | 1.4 |
| F14 | 6.56 | 149.9 | 7.0 |
| F15 | 5.48 | 119.6 | 5.1 |
| F16 | 5.39 | 100.6 | 2.8 |

TABLE 6

Round 2 Viscosity

| Sample | Actual pH | Actual Conc. (mg/mL) | Visc. (mPa * s) |
| --- | --- | --- | --- |
| F01 | 6.57 | 206.0 | 15.4 |
| F02 | 6.75 | 205.7 | 15.9 |
| F03 | 6.58 | 200.7 | 16.2 |
| F04 | 6.74 | 197.6 | 22.3 |
| F05 | 6.66 | 201.2 | 22.3 |
| F06 | 6.56 | 204.0 | 15.4 |

TABLE 6-continued

Round 2 Viscosity

| Sample | Actual pH | Actual Conc. (mg/mL) | Visc. (mPa * s) |
| --- | --- | --- | --- |
| F07 | 6.98 | 201.0 | 20.0 |
| F08 | 7.12 | 201.4 | 20.9 |
| F09 | 6.84 | 201.3 | 16.7 |
| F10 | 6.59 | 195.2 | 14.6 |
| F11 | 6.68 | 190.5 | 16.3 |
| F12 | 6.95 | 195.0 | 19.9 |
| F13 | 7.08 | 191.0 | 18.5 |
| F14 | 6.97 | 193.8 | 17.2 |
| F15 | 6.66 | 195.5 | 16.9 |
| F16 | 6.60 | 196.0 | 18.9 |
| F17 | 6.57 | 199.8 | 17.1 |
| F18 | 6.58 | 198.5 | 15.1 |

TABLE 7

Round 3 Viscosity

| Sample | Actual Conc. (mg/mL) | Temperature (° C.) | Shear Rate (1/s) | Visc. (mPa * s) |
| --- | --- | --- | --- | --- |
| F01 | 175.97 | 25 | 1000 | 10.81 |
| F01 | 206.91 | 25 | 1000 | 19.40 |
| F01 | 229.02 | 25 | 700 | 38.11 |
| F01 | 253.07 | 25 | 500 | 75.27 |
| F02 | 179.0 | 25 | 1000 | 9.63 |
| F02 | 201.7 | 25 | 1000 | 16.65 |
| F02 | 230.6 | 25 | 700 | 32.29 |
| F02 | 252.2 | 25 | 500 | 59.47 |

The viscosities were relatively low for all formulations in Round 1, even for those above 150 mg/mL protein (e.g., the viscosity of F09 was only 8.3 mPa*s at 166 mg/ml). Regarding the viscosity modulating effects of the excipients, Arg*HCl appeared to have the largest impact on viscosity reduction at equal concentration of protein. NaCl also appeared to reduce viscosity, although not as effectively as Arg*HCl. Formulations containing sorbitol as the tonicity modifier generally exhibited higher viscosities. The effects of pH and buffer on viscosity were not readily apparent. In general, the viscosity increased in a protein concentration dependent manner, apparently largely independent of pH.

In Round 2, it was found that lower pH values (in the range of 6.6-7.2) reduced the viscosity when the protein concentration was approximately 200 mg/mL. It was also found that Arg and NaCl were particularly effective at lowering viscosity. All Round 2 formulations exhibited viscosity values <23 cP, which is considered excellent for a monoclonal antibody at 200 mg/mL. FIG. 1 illustrates that the viscosities of these two formulations can be higher than 30 cp at certain concentrations.

Figure 2:
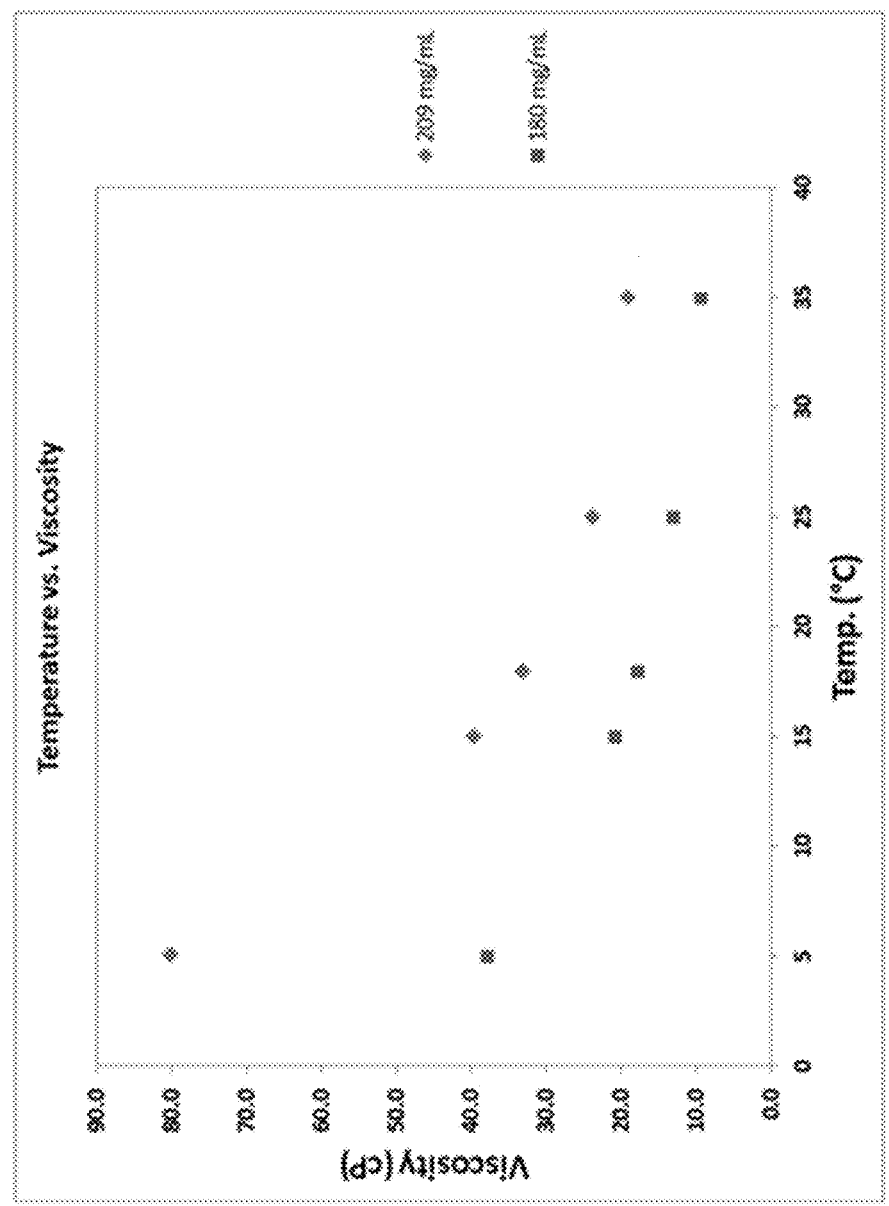
FIG. 2 depicts plot of viscosity over temperature of the formulation at 209 mg/mL and 180 mg/mL.

Viscosity of the drug substance in 20 mM L-histidine, 25 mM L-arginine hydrochloride, 125 mM sodium chloride, 0.05% (w/v) polysorbate 80, pH 6.6 was measured at various controlled temperatures (4° C., 15° C., 18° C., 25° C., and 35° C.). Three (3) data sets were measured for each temperature. Tabular results for samples analyzed at 208 mg/mL and at 180 mg/mL are outlined in Tables 8 and 9, respectively. FIG. 2 illustrates the change in viscosities of the two formulation samples over the range of temperatures indicated. As is shown in FIG. 2, viscosity results tested by rheometry at various controlled temperatures (4° C., 15° C., 18° C., 25° C., and 35° C.), at both 180 mg/mL and 209 mg/mL exhibited a significant decrease in viscosity with increasing temperature and/or lower active pharmaceutical ingradient (API) concentration.

TABLE 8

Viscosity of 208.8 mg/mL target protein concentration at varying temperatures
Viscosity by Rheometry at 208.8 mg/mL

| Temperature (° C.) | Test # | Speed (RPM) | Shear Stress (dyne/cm²) | Shear Rate (1/s) | Torque (%) | Viscosity (cP) |
|---|---|---|---|---|---|---|
| 5° C. | 1 | 2.5 | 14.81 | 18.8 | 62.9 | 79.1 |
|  | 2 | 3.0 | 18.07 | 22.5 | 78.5 | 80.0 |
|  | 3 | 3.5 | 21.27 | 26.3 | 92.5 | 81.0 |
| 15° C. | 1 | 6.5 | 19.01 | 48.8 | 82.4 | 39.4 |
|  | 2 | 7.0 | 20.88 | 52.5 | 90.7 | 39.8 |
|  | 3 | 7.5 | 22.28 | 56.3 | 96.8 | 39.7 |
| 18° C. | 1 | 7.5 | 18.55 | 56.3 | 80.6 | 33.0 |
|  | 2 | 8.2 | 20.23 | 61.5 | 87.8 | 32.9 |
|  | 3 | 8.6 | 21.50 | 64.5 | 93.5 | 33.3 |
| 25° C. | 1 | 12.0 | 21.15 | 90.0 | 91.9 | 23.5 |
|  | 2 | 12.2 | 21.70 | 91.5 | 94.3 | 23.8 |
|  | 3 | 12.4 | 22.23 | 93.0 | 96.7 | 23.9 |
| 35° C. | 1 | 15.0 | 21.01 | 112.5 | 91.3 | 18.9 |
|  | 2 | 15.5 | 21.84 | 116.3 | 94.8 | 18.9 |
|  | 3 | 16.0 | 23.02 | 120.0 | 99.2 | 19.1 |

TABLE 9

Viscosity of 180 mg/mL target protein concentration at varying temperatures
Viscosity by Rheometry at 180 mg/mL

| Temperature (° C.) | Test # | Speed (RPM) | Shear Stress (dyne/cm2) | Shear Rate (1/s) | Torque (%) | Viscosity (cP) |
|---|---|---|---|---|---|---|
| 5° C. | 1 | 7.3 | 20.51 | 54.8 | 88.9 | 37.5 |
|  | 2 | 7.5 | 21.15 | 56.3 | 91.8 | 37.6 |
|  | 3 | 7.7 | 21.82 | 57.8 | 94.9 | 37.8 |
| 15° C. | 1 | 13.0 | 20.03 | 97.5 | 87.1 | 20.6 |
|  | 2 | 13.5 | 20.97 | 101.3 | 91.2 | 20.7 |
|  | 3 | 14.0 | 21.82 | 105 | 94.9 | 20.8 |
| 18° C. | 1 | 15.0 | 19.93 | 112.5 | 86.7 | 17.6 |
|  | 2 | 15.5 | 20.58 | 116.3 | 89.7 | 17.7 |
|  | 3 | 16.0 | 21.22 | 120 | 92.3 | 17.7 |
| 25° C. | 1 | 20.0 | 19.50 | 150 | 84.3 | 13.0 |
|  | 2 | 20.7 | 19.91 | 155.3 | 86.9 | 12.8 |
|  | 3 | 21.4 | 20.67 | 160.5 | 90.0 | 12.9 |
| 35° C. | 1 | 30.0 | 20.72 | 225 | 90.1 | 9.2 |
|  | 2 | 31.0 | 21.45 | 232.5 | 93.2 | 9.2 |
|  | 3 | 32.0 | 22.46 | 240 | 97.5 | 9.4 |

Example 4: Stability of the Different Formulations Over a Course of 4 Weeks

Samples from Round 1 were tested to determine the effect of protein concentration, buffer species, pH, and inclusion of other excipients (Arg, NaCl, Sorbitol) on storage stability of the anti-OSMR antibody. Samples were analyzed after they were stored for two weeks at 40° C. (t2) or after they were stored for four weeks at 25° C. (t4). Initial osmolality of the samples from Round 1 are shown below in Table 10 and initial osmolality of the samples from Round 2 are shown below in Table 11. Actual pH values and protein concentrations of the samples from Round 1 and Round 2 are included above in Table 5 and Table 6, respectively. Protein precipitation was visible in the Round 1 F15 and F16 samples stored for 2 weeks at 40° C.

TABLE 10

Round 1 Osmolality

| Sample | Osmolality (mOsm/kg) |
|---|---|
| F01 | 336 |
| F02 | 340 |
| F03 | 341 |
| F04 | 363 |
| F05 | 319 |
| F06 | 345 |
| F07 | 357 |
| F08 | 359 |
| F09 | 315 |
| F10 | 388 |
| F11 | 334 |
| F12 | 351 |
| F13 | 341 |
| F14 | 423 |
| F15 | 372 |
| F16 | 349 |

TABLE 11

Round 2 Osmolality

| Sample | Osmolality (mOsm/kg) |
|---|---|
| F01 | 341 |
| F02 | 288 |
| F03 | 283 |
| F04 | N/A |
| F05 | N/A |
| F06 | 347 |
| F07 | N/A |
| F08 | N/A |
| F09 | 369 |
| F10 | 317 |
| F11 | 203 |
| F12 | N/A |
| F13 | N/A |
| F14 | 237 |
| F15 | 229 |
| F16 | 322 |
| F17 | 323 |
| F18 | 311 |

Monomer Purity

Size-exclusion chromatography was also performed on Round 1 and Round 2 samples to determine monomer purity at t0, after two weeks (t2) and after four weeks (t4), while Round 4 samples were tested for monomer purity at after freeze-thaw and agitation. Size exclusion chromatography (SEC) separates molecules based on their size by filtration through a gel. The gel consists of spherical beads containing pores of a specific size distribution. Separation occurs when molecules of different sizes are included or excluded from the pores within the matrix. Small molecules diffuse into the pores and their flow through the column is retarded according to their size, while large molecules do not enter the pores and are eluted in the column's void volume. Consequently, molecules separate based on their size as they pass through the column and are eluted in order of decreasing molecular weight (MW). Operating conditions and gel selection depend on the application and the desired resolution. Two common types of separations performed by SEC are fractionation and desalting (or buffer exchange.)

Exemplary monomer purity data comparing t0 and t2 at 40° C., t0 and t4 at 25° C. and t0 and t4 at 5° C. from Round 1 are provided in Table 12. Exemplary monomer purity data comparing t0 and t4 at 40° C., t0 and t4 at 25° C. and t0 and t4 at 5° C. from Round 2 are provided in Table 13.

Figure 3:
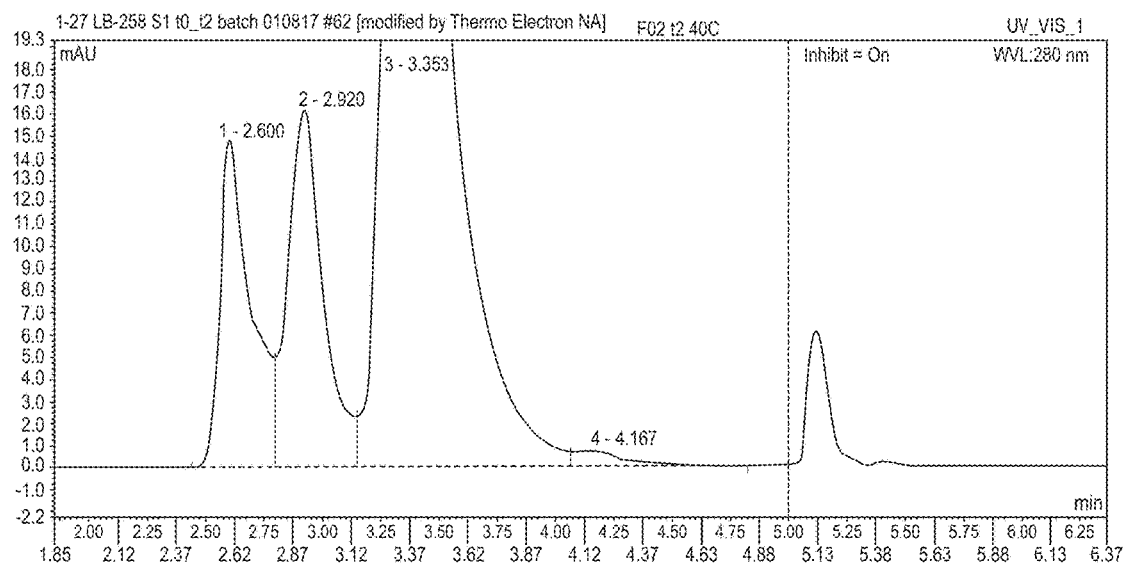
FIG. 3 depicts an exemplary chromatogram showing HMW species in a sample that was stressed by storage at 40° C.

Exemplary monomer purity data comparing agitated and freeze/thaw (F/T) samples to controls are provided in Table 14. The percentage of low molecular weight (LMW) species and high molecular weight (HMW) species in Round 1 and Round 2 samples was also determined by SEC. Exemplary LMW data comparing t0 and t2 from Round 1 are provided in Table 15. Exemplary LMW data comparing t0 and t4 from Round 2 at 25° C. are provided in Table 16. Exemplary LMW data comparing t0 and t4 from Round 2 at 5° C. are provided in Table 17. Exemplary HMW data comparing t0 and t2 from Round 1 are provided in Table 18. Exemplary HMW data comparing t0 and t4 at 25° C. from Round 1 are provided in Table 19. Exemplary HMW data comparing t0 and t4 at 5° C. from Round 1 are provided in Table 20. Exemplary HMW data comparing t0 and t2 at 40° C. from Round 2 are provided in Table 21. Exemplary HMW data comparing t0 and t4 from Round 2 at 25° C. are provided in Table 22. Exemplary HMW data comparing t0 and t4 from Round 2 at 5° C. are provided in Table 23. Exemplary HMW data comparing agitated and F/T samples to controls are provided in Table 24 and Table 25. An exemplary chromatogram showing HMW species in stressed samples (F02 at 40° C.) is presented in FIG. 3.

The SEC data from t2 of Round 1 indicate that the anti-OSMR antibody was prone to high molecular weight formation under stressed conditions and that the formation of low molecular weight species was minimal for most samples. The SEC data from t2 of Round 1 indicate that the highest monomer loss was observed in sample F04, when succinate was used at pH 6.0. In Round 1, the smallest monomer loss was observed in samples F05, F06 and F10, which contained histidine buffer with protein concentrations of 50, 100 and 125 mg/mL, respectively. At the protein concentration of 150 mg/mL, there was less monomer loss in samples containing sorbitol (F08 and F14), than in the sample with arginine (F03).

The SEC data from t4 at 25° C. for Round 1 indicate trends similar to those from the t2 data in that a higher loss of monomer was seen in formulations at pH≤6.0. Additionally, higher loss of monomer was seen in phosphate formulations at pH 7.2 and 7.6 (F07 and F13, respectively). Histidine and citrate formulations compared similarly in terms of monomer loss. Monomer loss was due almost solely HMW formation (primarily HMW 2). Negligible monomer loss was observed for almost all formulations stored at 2-8° C.

The SEC data from the agitation and F/T samples (Round 4) indicate that purity was effectively unchanged (vs. t0) for all samples except for the agitation samples that did not contain PS80. For these samples, there was an increase in both HMW 1 (aggregate) and HMW 2 (presumably dimer). These changes were much greater for F02 than F01.

TABLE 12

Round 1 Monomer Purity (%), at t0, t2 (40° C.), t4 (25° C.), and t4 (5° C.)

| Sample | t0 | t2 wk 40° C. | Δ t2 40° C. | t4 wk 25° C. | Δ t4 25° C. | t4 wk 5° C. | Δ t4 5° C. |
|---|---|---|---|---|---|---|---|
| F01 | 98.73 | 96.63 | 2.10 | 98.56 | 0.18 | 98.70 | 0.03 |
| F02 | 98.66 | 95.95 | 2.71 | 98.45 | 0.21 | 98.63 | 0.02 |
| F03 | 98.61 | 94.86 | 3.74 | 98.31 | 0.30 | 98.56 | 0.04 |
| F04 | 98.36 | 72.78 | 25.58 | 97.80 | 0.56 | 98.30 | 0.06 |
| F05 | 98.86 | 97.73 | 1.13 | 98.76 | 0.09 | 98.83 | 0.03 |
| F06 | 98.59 | 97.45 | 1.14 | 98.29 | 0.30 | 98.56 | 0.03 |
| F07 | 97.92 | 95.88 | 2.04 | 97.10 | 0.82 | 97.80 | 0.12 |
| F08 | 98.58 | 96.51 | 2.07 | 98.24 | 0.34 | 98.53 | 0.05 |

TABLE 12-continued

Round 1 Monomer Purity (%), at t0, t2 (40° C.), t4 (25° C.), and t4 (5° C.)

| Sample | t0 | t2 wk 40° C. | Δ t2 40° C. | t4 wk 25° C. | Δ t4 25° C. | t4 wk 5° C. | Δ t4 5° C. |
|---|---|---|---|---|---|---|---|
| F09 | 98.47 | 96.37 | 2.10 | 98.10 | 0.38 | 98.39 | 0.08 |
| F10 | 98.57 | 97.55 | 1.02 | 98.30 | 0.27 | 98.54 | 0.03 |
| F11 | 98.54 | 97.24 | 1.30 | 98.22 | 0.31 | 98.49 | 0.05 |
| F12 | 98.45 | 93.89 | 4.55 | 98.02 | 0.42 | 98.41 | 0.04 |
| F13 | 98.22 | 96.35 | 1.87 | 97.60 | 0.62 | 98.12 | 0.10 |
| F14 | 98.36 | 96.37 | 1.99 | 97.94 | 0.43 | 98.32 | 0.04 |
| F15 | 98.56 | Precipitated | Precipitated | 97.25 | 1.31 | 98.51 | 0.05 |
| F16 | 98.61 | Precipitated | Precipitated | 97.01 | 1.60 | 98.56 | 0.05 |

TABLE 13

Round 2 Monomer Purity (%), at t0, t2 (40° C.), t4 (25° C.), and t4 (5° C.)

| Sample | t0 | t2 wk 40° C. | Δ t2 40° C. | t4 wk 25° C. | Δ t4 25° C. | t4 wk 5° C. | Δ t4 5° C. |
|---|---|---|---|---|---|---|---|
| F01 | 98.48 | 91.41 | 7.07 | 98.08 | 0.40 | 98.42 | 0.05 |
| F02 | 98.43 | 93.74 | 4.69 | 98.05 | 0.37 | 98.31 | 0.12 |
| F03 | 98.35 | 93.31 | 5.05 | 97.81 | 0.54 | 98.22 | 0.14 |
| F06 | 98.48 | 91.56 | 6.92 | 98.06 | 0.42 | 98.45 | 0.03 |
| F09 | 98.10 | 94.71 | 3.39 | 97.47 | 0.63 | 97.98 | 0.12 |
| F10 | 98.27 | 92.55 | 5.72 | 97.72 | 0.55 | 98.12 | 0.15 |
| F11 | 98.58 | 95.06 | 3.52 | 98.11 | 0.47 | 98.48 | 0.10 |
| F14 | 98.44 | 95.60 | 2.84 | 97.94 | 0.49 | 98.30 | 0.14 |
| F15 | 98.62 | 94.98 | 3.64 | 98.24 | 0.38 | 98.54 | 0.08 |
| F16 | 98.40 | 94.66 | 3.75 | 97.79 | 0.61 | 98.34 | 0.06 |
| F17 | 98.45 | 91.90 | 6.55 | 97.78 | 0.67 | 98.30 | 0.15 |
| F18 | 98.66 | 91.47 | 7.19 | 98.31 | 0.36 | 98.56 | 0.10 |

TABLE 14

Round 4 Monomer Purity (%), for control, agitated and F/T samples

| Sample | Control | Agitated | Δ Agitated | 5x F/T | Δ 5x F/T |
|---|---|---|---|---|---|
| F01 PS80-free | 99.10 | 98.89 | 0.21 | 99.05 | 0.05 |
| F01 0.03% PS80 | 98.53 | 98.59 | −0.06 | 98.58 | −0.05 |
| F01 0.07% PS80 | 98.55 | 98.60 | −0.06 | 98.47 | 0.07 |
| F01 0.1% PS80 | 98.54 | 98.61 | −0.07 | 98.59 | −0.05 |
| F02 PS80-free | 99.14 | 98.07 | 1.07 | 99.15 | −0.01 |
| F02 0.03% PS80 | 98.71 | 98.62 | 0.09 | 98.68 | 0.03 |
| F02 0.07% PS80 | 98.63 | 98.61 | 0.03 | 98.59 | 0.04 |
| F02 0.1% PS80 | 98.63 | 98.67 | −0.04 | 98.69 | −0.06 |

TABLE 15

Round 1% LMW, t0 and t2 (40° C.)

| % LMW t0 | % LMW t2 wk | Δ LMW |
|---|---|---|
| 0.06 | 0.13 | 0.08 |
| 0.06 | 0.13 | 0.08 |
| 0.05 | 0.14 | 0.09 |
| 0.06 | 0.17 | 0.11 |
| 0.05 | 0.12 | 0.07 |
| 0.05 | 0.09 | 0.04 |
| 0.05 | 0.10 | 0.04 |
| 0.05 | 0.12 | 0.07 |
| 0.06 | 0.16 | 0.10 |
| 0.06 | 0.10 | 0.04 |
| 0.05 | 0.10 | 0.05 |
| 0.05 | 0.15 | 0.10 |
| 0.05 | 0.16 | 0.10 |
| 0.06 | 0.11 | 0.05 |

TABLE 15-continued

Round 1% LMW, t0 and t2 (40° C.)

| % LMW t0 | % LMW t2 wk | Δ LMW |
|---|---|---|
| 0.06 | Precipitated | Precipitated |
| 0.06 | Precipitated | Precipitated |

TABLE 16

Round 2% LMW, t0 and t4 (25° C.)

| Sample | % LMW t0 | % LMW t4 wk | Δ LMW |
|---|---|---|---|
| F01 | 0.05 | 0.04 | −0.01 |
| F02 | 0.03 | 0.03 | 0.00 |
| F03 | 0.03 | 0.04 | 0.00 |
| F06 | 0.04 | 0.06 | 0.02 |
| F09 | 0.04 | 0.05 | 0.01 |
| F10 | 0.03 | 0.03 | 0.00 |
| F11 | 0.03 | 0.05 | 0.02 |
| F14 | 0.03 | 0.04 | 0.01 |
| F15 | 0.03 | 0.04 | 0.01 |
| F16 | 0.03 | 0.05 | 0.01 |
| F17 | 0.02 | 0.05 | 0.03 |
| F18 | 0.03 | 0.04 | 0.00 |

TABLE 17

Round 2% LMW, t0 and t4 (5° C.)

| Sample | % LMW t0 | % LMW t4 wk | Δ LMW |
|---|---|---|---|
| F01 | 0.05 | 0.03 | −0.02 |
| F02 | 0.03 | 0.04 | 0.01 |
| F03 | 0.03 | 0.04 | 0.01 |
| F06 | 0.04 | 0.03 | −0.01 |
| F09 | 0.04 | 0.04 | 0.00 |
| F10 | 0.03 | 0.04 | 0.01 |
| F11 | 0.03 | 0.04 | 0.01 |
| F14 | 0.03 | 0.04 | 0.00 |
| F15 | 0.03 | 0.04 | 0.00 |
| F16 | 0.03 | 0.02 | −0.01 |
| F17 | 0.02 | 0.04 | 0.02 |
| F18 | 0.03 | 0.04 | 0.01 |

TABLE 18

Round 1 % HMW, t0 and t2 (40° C.)

| Sample | HMW 1 t0 | HMW 1 t2 wk | Δ HMW 1 | HMW 2 t0 | HMW 2 t2 wk | Δ HMW 2 |
|---|---|---|---|---|---|---|
| F01 | 0 | 1.25 | 1.25 | 1.21 | 1.99 | 0.78 |
| F02 | 0 | 1.76 | 1.76 | 1.28 | 2.16 | 0.88 |
| F03 | 0 | 2.63 | 2.63 | 1.34 | 2.37 | 1.03 |
| F04 | 0 | 23.75 | 23.75 | 1.58 | 3.31 | 1.72 |
| F05 | 0 | 0.50 | 0.50 | 1.09 | 1.65 | 0.56 |
| F06 | 0 | 0.29 | 0.29 | 1.35 | 2.17 | 0.82 |
| F07 | 0 | 0.36 | 0.36 | 2.02 | 3.67 | 1.64 |
| F08 | 0 | 0.74 | 0.74 | 1.37 | 2.63 | 1.26 |
| F09 | 0 | 0.91 | 0.91 | 1.47 | 2.57 | 1.10 |
| F10 | 0 | 0.27 | 0.27 | 1.37 | 2.07 | 0.70 |
| F11 | 0 | 0.38 | 0.38 | 1.41 | 2.28 | 0.87 |
| F12 | 0 | 2.69 | 2.69 | 1.50 | 3.27 | 1.77 |
| F13 | 0 | 0.40 | 0.40 | 1.73 | 3.09 | 1.36 |
| F14 | 0 | 0.69 | 0.69 | 1.58 | 2.83 | 1.25 |
| F15 | 0 | Precipitated | Precipitated | 1.38 | Precipitated | Precipitated |
| F16 | 0 | Precipitated | Precipitated | 1.33 | Precipitated | Precipitated |

TABLE 19

Round 1 % HMW, t0 and t4 (25° C.)

| Sample | HMW 1 t0 | HMW 1 t4 wk | Δ HMW 1 t4 | HMW 2 t0 | HMW 2 t4 wk | Δ HMW 2 t4 |
|---|---|---|---|---|---|---|
| F01 | 0 | 0.005 | 0.005 | 1.21 | 1.38 | 0.17 |
| F02 | 0 | 0.004 | 0.004 | 1.28 | 1.49 | 0.20 |
| F03 | 0 | 0.006 | 0.006 | 1.34 | 1.62 | 0.28 |
| F04 | 0 | 0 | 0.00 | 1.58 | 2.12 | 0.54 |
| F05 | 0 | 0 | 0.00 | 1.09 | 1.17 | 0.08 |
| F06 | 0 | 0 | 0.00 | 1.35 | 1.65 | 0.30 |
| F07 | 0 | 0 | 0.00 | 2.02 | 2.83 | 0.81 |
| F08 | 0 | 0 | 0.00 | 1.37 | 1.70 | 0.33 |
| F09 | 0 | 0.020 | 0.020 | 1.47 | 1.82 | 0.35 |
| F10 | 0 | 0.005 | 0.005 | 1.37 | 1.63 | 0.26 |
| F11 | 0 | 0.002 | 0.002 | 1.41 | 1.72 | 0.31 |
| F12 | 0 | 0 | 0.00 | 1.50 | 1.91 | 0.41 |
| F13 | 0 | 0.006 | 0.006 | 1.73 | 2.33 | 0.60 |
| F14 | 0 | 0 | 0.00 | 1.58 | 2.00 | 0.43 |
| F15 | 0 | 0.59 | 0.59 | 1.38 | 2.04 | 0.67 |
| F16 | 0 | 0.85 | 0.85 | 1.33 | 2.02 | 0.69 |

TABLE 20

Round 1 % HMW, t0 and t4 (5° C.)

| Sample | HMW 1 t0 | HMW 1 t4 wk | Δ HMW 1 t4 | HMW 2 t0 | HMW 2 t4 wk | Δ HMW 2 t4 |
|---|---|---|---|---|---|---|
| F01 | 0 | 0 | 0 | 1.21 | 1.25 | 0.04 |
| F02 | 0 | 0 | 0 | 1.28 | 1.32 | 0.04 |
| F03 | 0 | 0 | 0 | 1.34 | 1.39 | 0.05 |
| F04 | 0 | 0 | 0 | 1.58 | 1.65 | 0.07 |
| F05 | 0 | 0 | 0 | 1.09 | 1.12 | 0.03 |
| F06 | 0 | 0 | 0 | 1.35 | 1.39 | 0.04 |
| F07 | 0 | 0 | 0 | 2.02 | 2.15 | 0.13 |
| F08 | 0 | 0 | 0 | 1.37 | 1.42 | 0.05 |
| F09 | 0 | 0 | 0 | 1.47 | 1.56 | 0.09 |
| F10 | 0 | 0 | 0 | 1.37 | 1.41 | 0.04 |
| F11 | 0 | 0 | 0 | 1.41 | 1.46 | 0.04 |
| F12 | 0 | 0 | 0 | 1.50 | 1.55 | 0.05 |
| F13 | 0 | 0 | 0 | 1.73 | 1.82 | 0.10 |
| F14 | 0 | 0 | 0 | 1.58 | 1.63 | 0.05 |
| F15 | 0 | 0 | 0 | 1.38 | 1.43 | 0.05 |
| F16 | 0 | 0 | 0 | 1.33 | 1.37 | 0.04 |

TABLE 21

Round 2 % HMW, t0 and t2 (40° C.)

| Sample | HMW 1 t0 | HMW 1 t2 wk | Δ HMW 1 t2 | HMW 2 t0 | HMW 2 t2 wk | Δ HMW 2 t2 |
|---|---|---|---|---|---|---|
| F01 | 0 | 5.90 | 5.90 | 1.48 | 2.58 | 1.11 |
| F02 | 0 | 3.65 | 3.65 | 1.54 | 2.53 | 0.99 |
| F03 | 0 | 3.59 | 3.59 | 1.61 | 3.00 | 1.39 |
| F06 | 0 | 5.78 | 5.78 | 1.48 | 2.56 | 1.08 |
| F09 | 0 | 2.02 | 2.02 | 1.87 | 3.19 | 1.32 |
| F10 | 0 | 4.17 | 4.17 | 1.70 | 3.17 | 1.47 |
| F11 | 0 | 2.18 | 2.18 | 1.39 | 2.66 | 1.27 |
| F14 | 0 | 1.52 | 1.52 | 1.53 | 2.80 | 1.26 |
| F15 | 0 | 2.43 | 2.43 | 1.35 | 2.49 | 1.14 |
| F16 | 0 | 2.04 | 2.04 | 1.56 | 3.18 | 1.62 |
| F17 | 0 | 4.74 | 4.74 | 1.52 | 3.23 | 1.71 |
| F18 | 0 | 6.10 | 6.10 | 1.30 | 2.33 | 1.02 |

TABLE 22

Round 2 % HMW, t0 and t4 (25° C.)

| Sample | HMW 1 t0 | HMW 1 t4 wk | Δ % HMW 1 t4 | % HMW 2 t0 | % HMW 2 t4 wk | Δ HMW 2 t4 |
|---|---|---|---|---|---|---|
| F01 | 0 | 0 | 0 | 1.48 | 1.88 | 0.41 |
| F02 | 0 | 0 | 0 | 1.54 | 1.92 | 0.37 |
| F03 | 0 | 0 | 0 | 1.61 | 2.15 | 0.54 |
| F06 | 0 | 0 | 0 | 1.48 | 1.88 | 0.40 |
| F09 | 0 | 0 | 0 | 1.87 | 2.49 | 0.62 |
| F10 | 0 | 0 | 0 | 1.70 | 2.25 | 0.55 |
| F11 | 0 | 0 | 0 | 1.39 | 1.84 | 0.45 |
| F14 | 0 | 0 | 0 | 1.53 | 2.02 | 0.49 |
| F15 | 0 | 0 | 0 | 1.35 | 1.72 | 0.38 |
| F16 | 0 | 0 | 0 | 1.56 | 2.16 | 0.60 |
| F17 | 0 | 0 | 0 | 1.52 | 2.17 | 0.64 |
| F18 | 0 | 0 | 0 | 1.30 | 1.66 | 0.35 |

TABLE 23

Round 2 % HMW, t0 and t4 (5° C.)

| Sample | HMW 1 t0 | HMW 1 t4 wk | Δ % HMW 1 t4 | % HMW t0 | % HMW t4 wk | Δ HMW |
|---|---|---|---|---|---|---|
| F01 | 0 | 0 | 0 | 1.48 | 1.55 | 0.07 |
| F02 | 0 | 0 | 0 | 1.54 | 1.65 | 0.11 |
| F03 | 0 | 0 | 0 | 1.61 | 1.74 | 0.13 |
| F06 | 0 | 0 | 0 | 1.48 | 1.53 | 0.04 |
| F09 | 0 | 0 | 0 | 1.87 | 1.98 | 0.11 |
| F10 | 0 | 0 | 0 | 1.70 | 1.84 | 0.14 |
| F11 | 0 | 0 | 0 | 1.39 | 1.49 | 0.10 |
| F14 | 0 | 0 | 0 | 1.53 | 1.67 | 0.13 |
| F15 | 0 | 0 | 0 | 1.35 | 1.42 | 0.08 |
| F16 | 0 | 0 | 0 | 1.56 | 1.63 | 0.07 |
| F17 | 0 | 0 | 0 | 1.52 | 1.66 | 0.14 |
| F18 | 0 | 0 | 0 | 1.30 | 1.40 | 0.09 |

TABLE 24

Round 4% HMW 1 for control, agitated and F/T Samples

| Sample | HMW1 Control | HMW1 Agitated | HMW1 Δ Agitated | HMW1 5x F/T | HMW1 Δ 5x F/T |
|---|---|---|---|---|---|
| F01 PS80-free | 0.11 | 0.19 | 0.07 | 0.12 | 0.01 |
| F01 0.03% PS80 | 0 | 0 | 0 | 0 | 0 |
| F01 0.07% PS80 | 0 | 0 | 0 | 0 | 0 |
| F01 0.1% PS80 | 0 | 0 | 0 | 0 | 0 |
| F02 PS80-free | 0.14 | 0.65 | 0.51 | 0.12 | −0.02 |
| F02 0.03% PS80 | 0 | 0 | 0 | 0 | 0 |
| F02 0.07% PS80 | 0 | 0 | 0 | 0 | 0 |
| F02 0.1% PS80 | 0 | 0 | 0 | 0 | 0 |

TABLE 25

Round 4% HMW 2 for Control, Agitated and F/T Samples

| Sample | HMW2 Control | HMW2 Agitated | HMW2 Δ Agitated | HMW2 5x F/T | HMW2 Δ 5x F/T |
|---|---|---|---|---|---|
| F01 PS80-free | 0.75 | 0.89 | 0.15 | 0.80 | 0.05 |
| F01 0.03% PS80 | 1.45 | 1.40 | −0.05 | 1.41 | −0.04 |
| F01 0.07% PS80 | 1.44 | 1.39 | −0.05 | 1.51 | 0.07 |
| F01 0.1% PS80 | 1.44 | 1.38 | −0.06 | 1.14 | −0.04 |
| F02 PS80-free | 0.69 | 1.24 | 0.55 | 0.70 | 0.01 |
| F02 0.03% PS80 | 1.28 | 1.36 | 0.08 | 1.31 | 0.03 |
| F02 0.07% PS80 | 1.35 | 1.37 | 0.02 | 1.39 | 0.05 |
| F02 0.1% PS80 | 1.35 | 1.32 | −0.03 | 1.31 | −0.05 |

Figure 4:
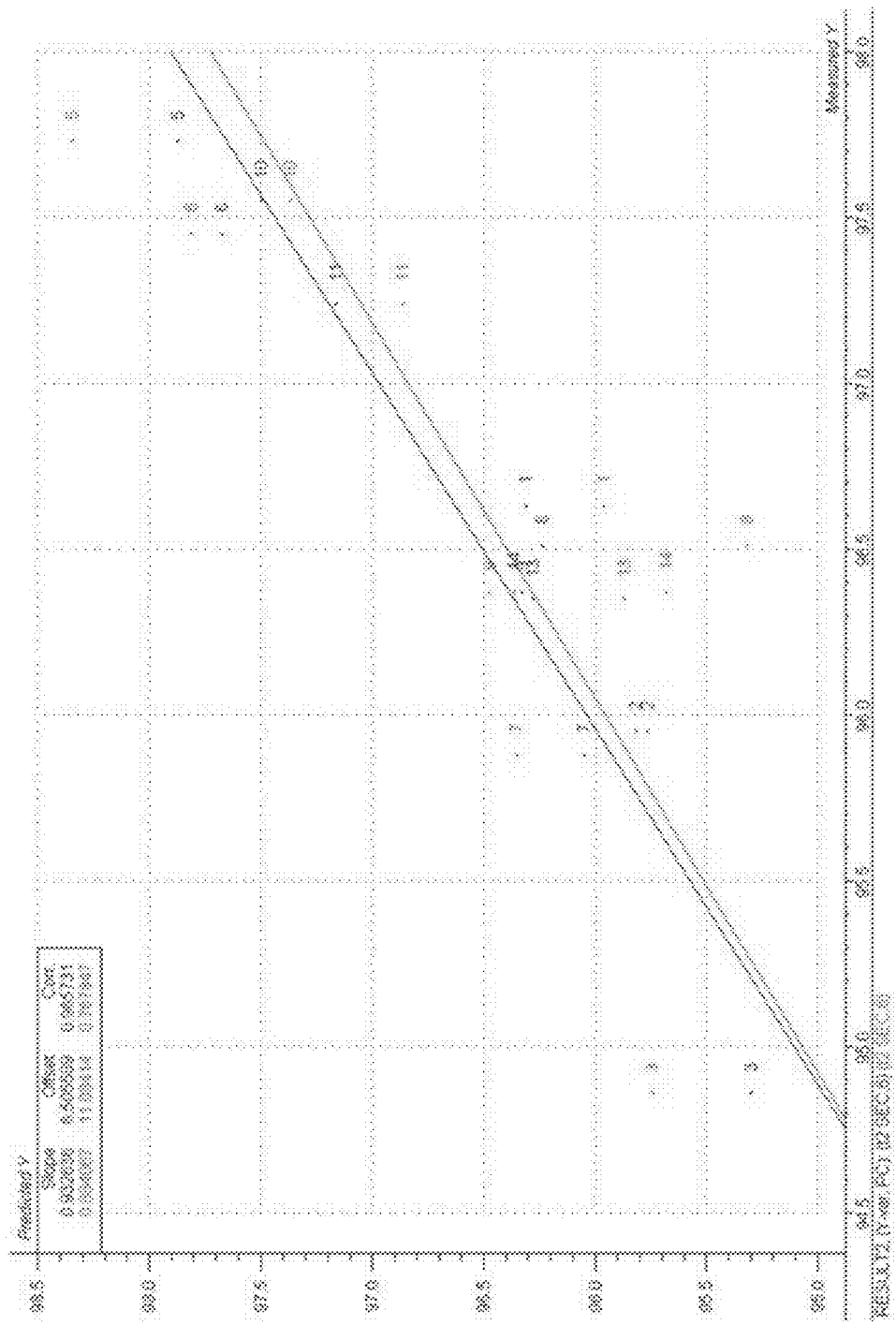
FIG. 4 depicts an exemplary graph showing predicted vs. measured monomer content. A partial least squares regression was performed to model monomer content in samples after two weeks at 40° C.

A partial least squares regression was performed to model monomer content at t2 (samples after two weeks at 40° C.). FIG. 4 shows an exemplary graph depicting predicted vs. measured monomer content.

In Round 1 experiments, the data indicated that formulation 4 may not be representative. The data indicate that histidine appears to be stabilizing in this model, while citrate and phosphate showed little ability to maintain monomer content. Additionally, while arginine appears to destabilize the protein at a higher storage temperature (40° C.), it was protective or stabilizing at lower storage temperatures (25° C. or lower). Sorbitol was seen to have little effect on the stability of the antibody. NaCl appeared to be the best stabilizer of those tested. Storage stability appeared to be constant up to a protein concentration of approximately 100 mg/mL, but it decreased above that concentration. Indeed, similar to Round 1, the SEC data from Round 2 indicates that the propensity of the antibody to aggregate increases with higher concentrations of the antibody, as the amount of HMW components formed for these Round 2 formulations (200 mg/mL) is greater than those measured for comparable, lower protein concentration formulations from Round 1.

Charge Distribution

The purity of the main charge variant (main peak) for the samples from Round 1 and Round 2 was determined by capillary isoelectric focusing (cIEF). cIEF was conducted using the Beckman Coulter kit method on a PA 800 Plus instrument. cIEF data from Round 1 of the percentage of the main peak at t0, after two weeks at 40° C. (t2) and after four weeks at 25° C. (t4) are shown below in Table 26. cIEF data from Round 2 of the percentage of the main peak at t0, after two weeks at 40° C. (t2) and after four weeks at 25° C. (t4) are shown below in Table 27.

In general, loss of the main isoform was correlated with the pH of the formulations. Higher pH formulations had a greater loss of main isoform at both t2/40° C. and t4/25° C., with the loss mainly manifesting itself as an increase in acidic charge forms. An exception in Round 1 was F04 (pH 6.0) at t2, which showed a loss of main peak to both acidic and basic sides of the main peak.

TABLE 26

Round 1 % main peak, t0, t2 and t4

| Sample | Buffer | pH | % Main Peak t0 | t2 wk 40° C. | Δ t2 | % Main Peak t0 | t4 wk 25° C. | Δ t4 |
|---|---|---|---|---|---|---|---|---|
| F01 | citrate | 6.60 | 51.2 | 43.5 | 7.7 | 51.2 | 51.0 | 0.2 |
| F02 | citrate | 6.59 | 50.9 | 43.5 | 7.4 | 50.9 | 50.7 | 0.2 |
| F03 | citrate | 6.57 | 50.6 | 42.7 | 7.9 | 50.6 | 49.9 | 0.7 |
| F04 | succinate | 6.01 | 49.0 | 36.8 | 12.2 | 49.0 | 48.8 | 0.2 |
| F05 | His | 6.57 | 48.5 | 41.6 | 6.9 | 48.5 | 49.4 | −0.9 |
| F06 | His | 6.89 | 49.6 | 40.7 | 8.9 | 49.6 | 48.3 | 1.3 |
| F07 | phos | 7.17 | 50.5 | 33.1 | 17.4 | 50.5 | 46.2 | 4.3 |
| F08 | His | 6.60 | 50.5 | 41.8 | 8.7 | 50.5 | 51.0 | −0.5 |
| F09 | His | 7.50 | 50.1 | 34.5 | 15.6 | 50.1 | 46.1 | 4.0 |
| F10 | His | 7.19 | 50.3 | 40.3 | 10.0 | 50.3 | 49.5 | 0.8 |
| F11 | phos | 6.54 | 51.2 | 42.2 | 9.0 | 51.2 | 51.5 | −0.3 |
| F12 | phos | 6.09 | 51.4 | 41.4 | 10.0 | 51.4 | 51.5 | −0.1 |
| F13 | phos | 7.47 | 49.9 | 28.0 | 21.9 | 49.9 | 45.5 | 4.4 |
| F14 | succinate | 6.56 | 51.0 | 43.4 | 7.6 | 51.0 | 51.8 | −0.8 |

TABLE 26-continued

Round 1 % main peak, t0, t2 and t4

| Sample | Buffer | pH | % Main Peak | | | % Main Peak | | |
|---|---|---|---|---|---|---|---|---|
| | | | t0 | t2 wk 40° C. | Δ t2 | t0 | t4 wk 25° C. | Δ t4 |
| F15 | citrate | 5.48 | 50.5 | Precipitate | Precipitate | 50.5 | 49.0 | 1.5 |
| F16 | succinate | 5.39 | 52.0 | Precipitate | Precipitate | 51.7 | 48.0 | 3.7 |

TABLE 27

Round 2 % main peak, t0, t2 and t4

| Sample | pH | % Main Peak | | | % Main Peak | | |
|---|---|---|---|---|---|---|---|
| | | t0 | t2 wk 40° C. | Δ t2 | t0 | t4 wk 25° C. | Δ t4 |
| F01 | 6.57 | 51.1 | 42.4 | 8.7 | 51.1 | 50.6 | 0.5 |
| F02 | 6.75 | 50.8 | 44.4 | 6.4 | 50.8 | 48.8 | 2.0 |
| F03 | 6.58 | 50.9 | 42.6 | 8.3 | 50.9 | 49.6 | 1.3 |
| F06 | 6.56 | 50.7 | 44.2 | 6.5 | 50.7 | 50.1 | 0.6 |
| F09 | 6.84 | 50.5 | 45.2 | 5.3 | 50.5 | 49.4 | 1.1 |
| F10 | 6.59 | 51.1 | 45.0 | 6.1 | 51.1 | 49.2 | 1.9 |
| F11 | 6.68 | 50.3 | 44.4 | 5.9 | 50.3 | 49.2 | 1.1 |
| F14 | 6.97 | 49.8 | 39.1 | 10.7 | 49.8 | 47.0 | 2.8 |
| F15 | 6.66 | 50.3 | 43.9 | 6.4 | 50.3 | 49.0 | 1.3 |
| F16 | 6.60 | 49.6 | 43.7 | 5.9 | 49.6 | 48.7 | 0.9 |
| F17 | 6.57 | 49.4 | 42.1 | 7.3 | 49.4 | 48.7 | 0.7 |
| F18 | 6.58 | 50.4 | 44.3 | 6.1 | 50.4 | 48.8 | 1.6 |

Figure 5:
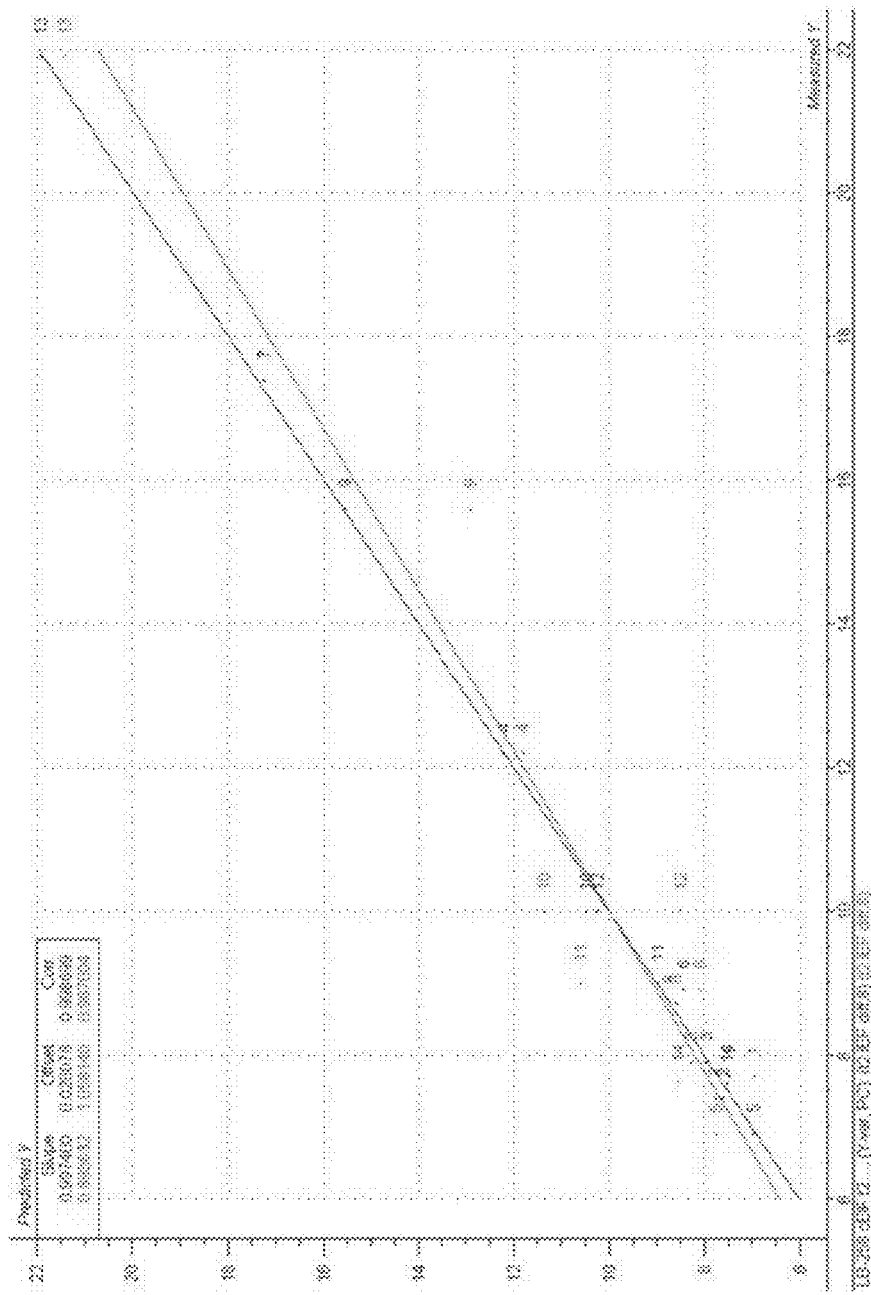
FIG. 5 depicts an exemplary graph showing predicted vs. measured capillary isoelectric focusing (cIEF) difference in main peak percentage. A partial least squares regression was performed to model cIEF difference in main peak percentage data from Round 1 in samples after two weeks at 40° C.
Figure 6:
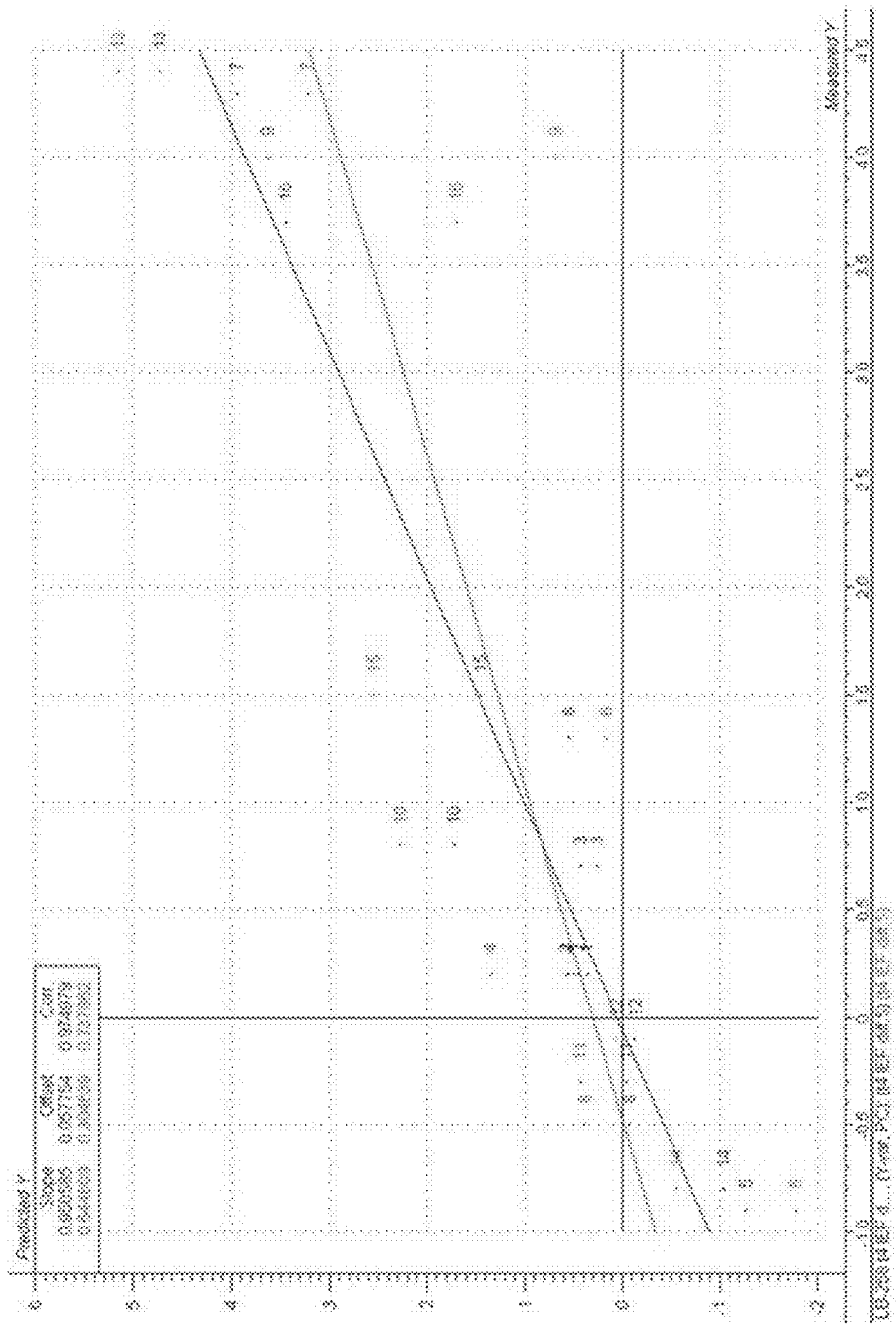
FIG. 6 depicts an exemplary graph showing predicted vs. measured cIEF difference in main peak percentage. A partial least squares regression was performed to model cIEF difference in main peak percentage data from Round 1 in samples after four weeks at 25° C.
Figure 7:
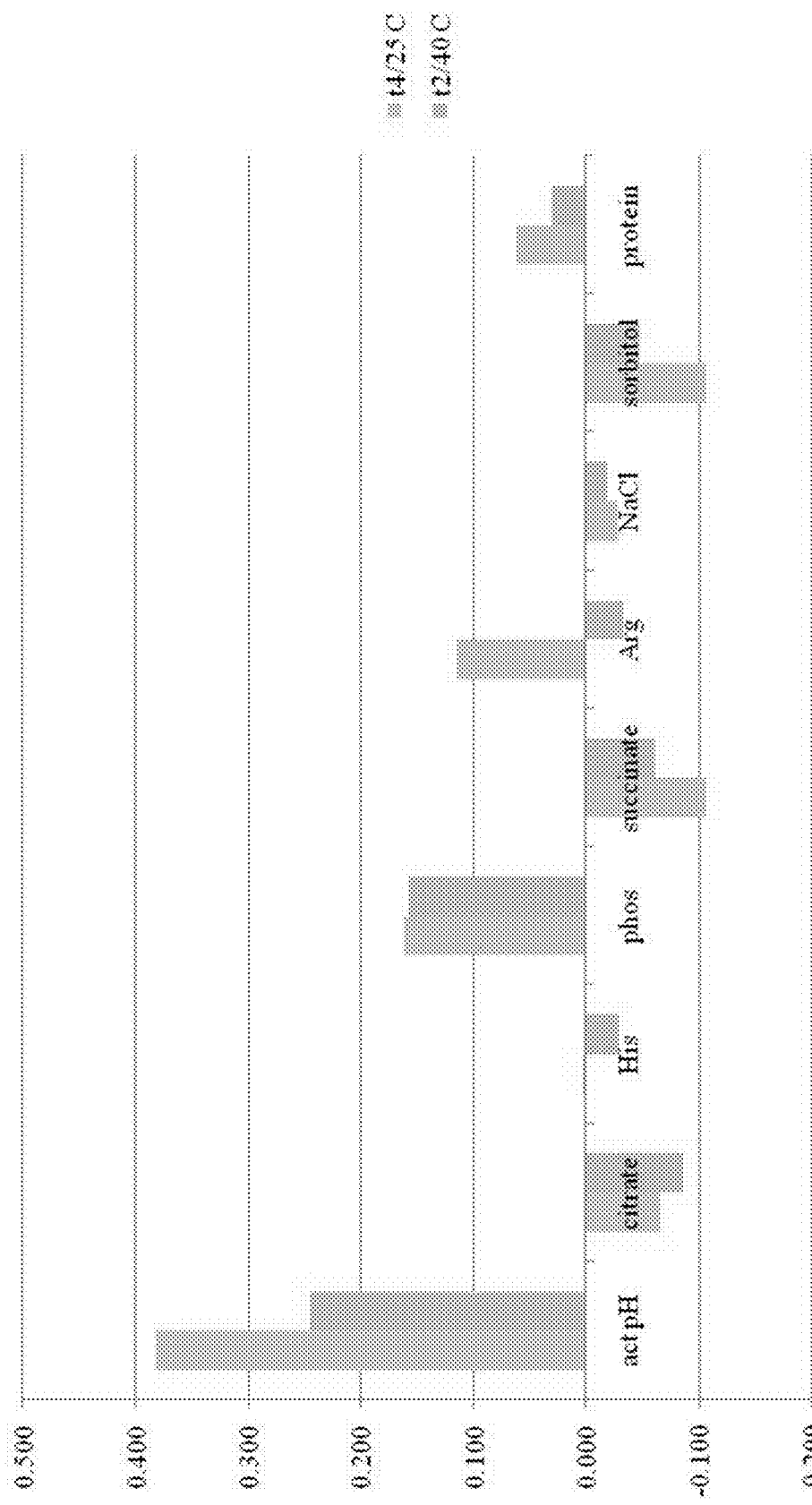
FIG. 7 depicts exemplary correlation coefficients for various Round 1 formulation variables at t2 (samples were stored for two weeks at 40° C.) and t4 (samples were stored for four weeks at 25° C.).

A partial least squares regression was performed to model cIEF difference in main peak percentage data from Round 1 at both t2 (samples after two weeks at 40° C.) and t4 (samples after four weeks at 25° C.). The model for t2 only used data from formulations 1-13. A partial least-squares (PLS) model generated from the t2/40° C. data demonstrated the stabilization afforded by NaCl compared to an excipient like mannitol. FIG. 5 shows an exemplary graph depicting predicted vs. measured cIEF difference in main peak percentage at t2. FIG. 6 shows an exemplary graph depicting predicted vs. measured cIEF difference in main peak percentage at t4. The correlation coefficients for the various formulation variables at t2 and t4 are shown in FIG. 7.

Susceptibility to Interfacial Damage

Samples from Round 4 were tested to determine the susceptibility of the anti-OSMR antibody (formulated with varying levels of PS80) to interfacial damage when exposed to freeze-thaw (F/T) and agitation stresses. F/T studies were conducted by freezing samples at −80° C. for ≥17 hours followed by thawing at room temperature for approximately 4 hours. Samples were mixed (by swirling) between freeze thaw cycles. A total of 5 F/T cycles were performed. Agitation was conducted by shaking at 590 rpm (on an orbital shaker, 3 mm orbit) for 24 hours at 25° C. For both the F/T and agitation studies, the container/closure consisted of a 1 mL Type 1 glass vial with Fluorotec stopper. The fill volume was 400 µL and the vial orientation was vertical and horizontal for the F/T and agitation study, respectively.

Two formulations were chosen to conduct this study (based upon their viscosity and stability profiles), and their compositions are listed above in Table 4. The measured PS80 content for each sample is given below in Table 28. The results of these analyses are summarized below. PS80 content for each formulation was determined using a PS80 assay consisting of free oleic acid determination using RP-HPLC to indirectly determine PS80 content. Free oleic acid was obtained by hydrolyzing the PS80 contained within a given formulation. This free oleic acid was then analyzed via Reversed-Phase High-Performance Liquid Chromatography (RP-HPLC) and concentration was determined against a standard curve generated with PS80 standards (hydrolyzed to obtained free oleic acid) prepared from the same PS80 (here JT Baker) used to prepare a given formulation. The standard curve consisted of 5 PS80 concentrations ranging from 0.0005-0.005% (w/v) PS80.

TABLE 28

Round 4 Measured PS80 Content

| Sample | Measured PS80 Content (% w/v) |
|---|---|
| F01 PS80-free | N/A |
| F01 0.03% PS80 | 0.027 |
| F01 0.07% PS80 | 0.068 |
| F01 0.1% PS80 | 0.095 |
| F02 PS80-free | N/A |
| F02 0.03% PS80 | 0.027 |
| F02 0.07% PS80 | 0.065 |
| F02 0.1% PS80 | 0.091 |

Protein content obtained from UV-absorbance at 280 nm (A280) for the agitation and F/T samples is shown below in Table 29. Protein content for all samples was unchanged (within the error of the measurement) compared to the starting material (pre-PS80 material), indicating that significant amounts of precipitation that would be capable of changing protein concentration did not occur for these samples.

TABLE 29

Round 4 protein content (mg/mL)

| Sample | Starting Material (mg/mL) | Agitated (mg/mL) | 5x F/T |
|---|---|---|---|
| F01 PS80-free | 191.42 | 191.60 | 190.01 |
| F01 0.03% PS80 | 188.23 | 194.10 | 193.26 |
| F01 0.07% PS80 | 188.23 | 194.71 | 192.81 |
| F01 0.1% PS80 | 188.23 | 194.01 | 191.14 |
| F02 PS80-free | 186.73 | 188.29 | 186.76 |
| F02 0.03% PS80 | 195.24 | 201.25 | 195.72 |
| F02 0.07% PS80 | 195.24 | 204.66 | 198.88 |
| F02 0.1% PS80 | 195.24 | 198.01 | 194.62 |

Round 4 studies, including additional sub-visible particle (SVP) and dynamic light scattering (DLS) analyses (data not shown) indicated that the anti-OSMR antibody was, under certain conditions, prone to particle formation in the absence of PS80. In particular, the molecule appears to be most prone to particle formation during agitation processes. In samples lacking PS80, the SEC results show that F01, which contains NaCl, was able to suppress the formation of impurities to a greater extent than F02, which lacks NaCl. Inclusion of PS80 at just 0.03% (w/v) was shown to be sufficient in protecting against the formation of aggregates. F01 and F02 formulations with PS80 at 0.03%, 0.07% and 0.1% (w/v) were shown by SEC and SVP to protect against aggregate formation to a similar extent. Additionally, upon agitation, the F01 formulations appeared to be less prone to SVP formation (total particle counts) compared to F02 formulations.

Example 5: Drug Substance Stability Over Extended Period at Different Incubation Temperatures This example illustrates that the anti-OSRMβ antibody in formulation buffer (20 mM L-histidine, 25 mM L-arginine hydrochloride, 125 mM sodium chloride, 0.05% (w/v) polysorbate 80, pH 6.6) is stable at temperature of −70° C. or 5° C., at least to 3 months. Samples were pulled from storage at different temperatures and the various characteristics were examined. FIG. 8 illustrates observed characteristics of two exemplary samples pulled for examination at indicated time periods from the storage temperature of −70° C. and 5° C. relative to the baseline (time=0). FIG. 9 illustrates observed characteristics of two exemplary samples pulled at indicated time periods from the storage temperature of 25° C. (accelerated), and 40° C. (stressed conditions) relative to the baseline. Size exclusion chromatography (SEC) results over the period of three months at different temperatures of storage, −70° C. and 5° C., (FIG. 8) as well as at accelerated conditions by storage at 25° C. (FIG. 9) indicate the relative amount of aggregates were repeatedly less than 5% for as long as 3 months. Additionally, the formulation samples were analyzed by non-reducing capillary gel electrophoresis (CE-SDS (NR)) over a period of three months at the indicated times to detect intact IgG monomers and fragments of IgG as a measure of stability of the formulation. Non-reducing SDS data in the figures indicate greater than 90% of the antibody (drug substance) existed as intact monomers at storage temperatures of −70° C. and 5° C., (FIG. 8) as well as at accelerated conditions by storage at 25° C. for the period of 3 months. With storage at 40° C. (FIG. 9), however, samples showed higher percentage of aggregates and lower percent of intact IgG monomers.

Example 6: Drug Substance Production Stress—Robustness Analysis

In this exemplary study, a freeze/thaw profile was generated using a placebo (20 mM L-Histidine, 25 mM L-Arginine-HCl, 125 mM NaCl, 0.05% PS80, pH 6.6) within a Sartorius Celsius Flexible Freeze and Thaw (FFT) container. Based on the freeze/thaw profile, the drug substance in formulation buffer (20 mM L-histidine, 25 mM L-arginine hydrochloride, 125 mM sodium chloride, 0.05% (w/v) polysorbate 80, pH 6.6-6.8) was subjected to repeated freeze/thaw cycles and placed at 25° C. in order to assess the robustness of the formulation following stress conditions relevant in drug substance production.

During this drug substance production stress study, the drug substance was stressed by being subjected to three (3) consecutive freeze/thaw cycles, followed by three (3) months incubation at 25° C. An additional sample (Control) of the formulation remained at 2-8° C. to serve as an unstressed control.

After being stressed by three (3) cycles of controlled freezing and thawing, the API in the current formulation did not exhibit significant differences from an unstressed Control by visual appearance, pH, API concentration, SE-UPLC, IE-HPLC, or MFI.

After 3 months of incubation at 25° C., no differences in visual appearance, pH, or API concentration were noted between the stressed samples and the control samples. Slight physical degradation was observed by SE-UPLC, which was orthogonally supported by CE-SDS. The stressed sample exhibited increases in sub-visible particle counts compared to the control by MFI. Slight chemical modification was observed by IE-HPLC. These degradations are likely due to thermal stress and not the result of the Freeze-Thaw cycling. Main degradants were identified as aggregate species by SE-UPLC and acidic species by IE-HPLC.

Example 7: In-Use Compatibility of Drug Product

In this exemplary study, 1 mL of the drug product was drawn into disposable 3-cc and 1-cc sterile syringes via a 21G 1½" needle. The filled syringes were then incubated with the needle attached at 25° C.±2° C. and 5±3° C. stability chambers and analyzed at six (6) time points: 0, 1, 4, 8, 16 and 24 hours. At each time point, the drug was expelled from the syringes through a 27G ½" needle into a sterile 2 cc vial. Expelled samples were analyzed immediately by visual appearance, concentration, SEC, and MFI. All samples were free of visible particles. The visual observations remained unchanged by the temperature storage conditions or storage duration. Regardless of syringe size or incubation temperature, the API concentration for all samples remained at or near ($\Delta \leq 2.3\%$) the target concentration.

Also, regardless of syringe size, no significant changes in chromatographic profiles or peak percentages were detected following 24 hours of incubation at either 5° C. or 25° C., in comparison to time zero values. Results were comparable to time zero values as well to the unstressed control samples.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A stable formulation comprising an anti-oncostatin M receptor (OSMR) antibody and having a pH ranging from approximately 6.0-7.6,
    wherein the formulation comprises 10-150 mM arginine, 10-20 mM histidine, or 5-75 mM phosphate,
    wherein the anti-OSMR antibody has a pI ranging from 6.5-8.0 and is present in the formulation at a concentration ranging from 100-250 mg/ml, and
    wherein at least 90% of the anti-OSMR antibody exists as monomer in the formulation upon storage at 40° C. for two weeks wherein the anti-OSMR antibody comprises (i) a heavy chain having the amino acid sequence set forth in SEQ ID NO: 1; and a light chain having the amino acid sequence set forth in SEQ ID NO: 2; or (ii) a heavy chain variable domain having the amino acid sequence set forth in SEQ ID NO: 3; and a light chain variable domain having the amino acid sequence set forth in SEQ ID NO: 4.

2. The stable formulation of claim 1, wherein upon storage at 25° C. for 4 weeks, the relative amount of high molecular weight (HMW) species in the formulation increases between 0.3% and 0.7%.

3. The stable formulation of claim 1, wherein upon storage at 25° C. for 3 months, the relative amount of HMW species in the formulation increases between 0.3% and 5%.

4. The stable formulation of claim 1, wherein the formulation further comprises NaCl at a concentration ranging from 25-250 mM.

5. The stable formulation of claim 4, wherein the molar ratio of NaCl to arginine is at least 1.

6. The stable formulation of claim 5, wherein the molar ratio of NaCl to arginine is approximately 1:1, 1.5:1, 3:1, or 5:1.

7. The stable formulation of claim 6, wherein the molar ratio of NaCl to arginine is 5:1.

8. The stable formulation of claim 7, wherein the formulation comprises 125 mM NaCl and 25 mM arginine.

9. The stable formulation of claim 8, wherein the formulation comprises:
    175-250 mg/ml of anti-OSMR antibody,
    25 mM arginine,
    20 mM histidine,
    125 mM NaCl,
    0.05% (w/v) polysorbate 80 (P80), and
    pH of 6.6.

10. The stable formulation of claim 9, wherein the formulation comprises 180 mg/ml of anti-OSMR antibody.

11. The stable formulation of claim 9, wherein the formulation comprises 210 mg/ml of anti-OSMR antibody.

12. The stable formulation of claim 1, wherein at least 95% of the anti-OSMR antibody exists as monomer.

13. The stable formulation of claim 1, wherein less than 5% of the anti-OSMR antibody exists as HMW species.

14. The stable formulation of claim 1, wherein the formulation has a viscosity of less than 50 mPa*s measured by a microfluidic rheometer.

15. The stable formulation of claim 1, wherein the formulation has a viscosity of less than 30 mPa*s measured by a microfluidic rheometer.

16. The stable formulation of claim 1, wherein the amount of HMW species in the formulation increases less than 5% upon storage at 25° C. for 4 weeks.

17. The stable formulation of claim 16, wherein the amount of HMW species in the formulation increases less than 2% upon storage at 25° C. for 4 weeks.

18. A stable formulation comprising an anti-oncostatin M receptor (OSMR) antibody, wherein the formulation has a pH in a range of 6.0-7.6 and comprises:

100-250 mg/ml of the anti-OSMR antibody,
10-150 mM arginine,
10-20 mM histidine, and
25-250 mM NaCl.

19. The stable formulation of claim 18, wherein the anti-OSMR antibody has a pI ranging from 6.5-8.0.

* * * * *

SEQUENCE LISTING

```
<160> NUMBER OF SEQ ID NOS: 16

<210> SEQ ID NO 1
<211> LENGTH: 452
<212> TYPE: PRT
<213> ORGANISM: Unknown
<220> FEATURE:
<223> OTHER INFORMATION: Anti-OSMR Heavy Chain Amino Acid Sequence

<400> SEQUENCE: 1

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
                20                  25                  30

Glu Ile Asn Trp Val Arg Gln Ala Thr Gly Gln Gly Leu Glu Trp Met
                35                  40                  45

Gly Trp Met Asn Pro Asn Ser Gly Tyr Thr Gly Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Met Ser Ser Leu Arg Ser Glu Asp Thr Ala Val Tyr Tyr Cys
                85                  90                  95

Ala Arg Asp Ile Val Ala Ala Asn Thr Asp Tyr Tyr Phe Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
        210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Gln Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
    450

<210> SEQ ID NO 2
<211> LENGTH: 216
<212> TYPE: PRT
<213> ORGANISM: Unknown
<220> FEATURE:
<223> OTHER INFORMATION: Anti-OSMR Light Chain Amino Acid Sequence

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr His Gln Leu Pro Gly Thr Ala Pro Lys Leu Leu
        35                  40                  45

Ile Tyr Asn Ile Asn Lys Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ser Thr Trp Asp Asp Ser Leu
                85                  90                  95

Asp Gly Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 3
<211> LENGTH: 126
<212> TYPE: PRT
<213> ORGANISM: Unknown
<220> FEATURE:
<223> OTHER INFORMATION: Anti-OSMR Heavy Chain Variable Domain Amino
      Acid Sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Glu Ile Asn Trp Val Arg Gln Ala Thr Gly Gln Gly Leu Glu Trp Met
        35                  40                  45

Gly Trp Met Asn Pro Asn Ser Gly Tyr Thr Gly Tyr Ala Gln Lys Phe

```
                    50                  55                  60
Gln Gly Arg Val Thr Met Thr Arg Asp Thr Ser Ile Ser Thr Ala Tyr
 65                  70                  75                  80

Met Glu Met Ser Ser Leu Arg Ser Glu Asp Thr Ala Val Tyr Tyr Cys
                 85                  90                  95

Ala Arg Asp Ile Val Ala Ala Asn Thr Asp Tyr Tyr Phe Tyr Tyr Gly
             100                 105                 110

Met Asp Val Trp Gly Gln Gly Thr Thr Val Thr Val Ser Ser
        115                 120                 125
```

<210> SEQ ID NO 4
<211> LENGTH: 111
<212> TYPE: PRT
<213> ORGANISM: Unknown
<220> FEATURE:
<223> OTHER INFORMATION: Anti-OSMR Light Chain Variable Domain Amino
      Acid Sequence

<400> SEQUENCE: 4

```
Gln Ser Val Leu Thr Gln Pro Pro Ser Ala Ser Gly Thr Pro Gly Gln
 1               5                  10                  15

Arg Val Thr Ile Ser Cys Ser Gly Ser Asn Ser Asn Ile Gly Ser Asn
             20                  25                  30

Thr Val Asn Trp Tyr His Gln Leu Pro Gly Thr Ala Pro Lys Leu Leu
         35                  40                  45

Ile Tyr Asn Ile Asn Lys Arg Pro Ser Gly Val Pro Asp Arg Phe Ser
 50                  55                  60

Gly Ser Lys Ser Gly Ser Ala Ser Leu Ala Ile Ser Gly Leu Gln
 65                  70                  75                  80

Ser Glu Asp Glu Ala Asp Tyr Tyr Cys Ser Thr Trp Asp Asp Ser Leu
                 85                  90                  95

Asp Gly Val Val Phe Gly Gly Gly Thr Lys Leu Thr Val Leu Gly
             100                 105                 110
```

<210> SEQ ID NO 5
<211> LENGTH: 5
<212> TYPE: PRT
<213> ORGANISM: Unknown
<220> FEATURE:
<223> OTHER INFORMATION: HCDR1 amino acid sequence

<400> SEQUENCE: 5

```
Ser Tyr Glu Ile Asn
 1               5
```

<210> SEQ ID NO 6
<211> LENGTH: 21
<212> TYPE: PRT
<213> ORGANISM: Unknown
<220> FEATURE:
<223> OTHER INFORMATION: HCDR2 amino acid sequence

<400> SEQUENCE: 6

```
Trp Met Gly Trp Met Asn Pro Asn Ser Gly Tyr Thr Gly Tyr Ala Gln
 1               5                  10                  15

Lys Phe Gln Gly Arg
             20
```

<210> SEQ ID NO 7
<211> LENGTH: 17
<212> TYPE: PRT

-continued

```
<213> ORGANISM: Unknown
<220> FEATURE:
<223> OTHER INFORMATION: HCDR3 amino acid sequence

<400> SEQUENCE: 7

Asp Ile Val Ala Ala Asn Thr Asp Tyr Tyr Phe Tyr Tyr Gly Met Asp
1               5                   10                  15

Val

<210> SEQ ID NO 8
<211> LENGTH: 13
<212> TYPE: PRT
<213> ORGANISM: Unknown
<220> FEATURE:
<223> OTHER INFORMATION: LCDR1 amino acid sequence

<400> SEQUENCE: 8

Ser Gly Ser Asn Ser Asn Ile Gly Ser Asn Thr Val Asn
1               5                   10

<210> SEQ ID NO 9
<211> LENGTH: 7
<212> TYPE: PRT
<213> ORGANISM: Unknown
<220> FEATURE:
<223> OTHER INFORMATION: LCDR2 amino acid sequence

<400> SEQUENCE: 9

Asn Ile Asn Lys Arg Pro Ser
1               5

<210> SEQ ID NO 10
<211> LENGTH: 11
<212> TYPE: PRT
<213> ORGANISM: Unknown
<220> FEATURE:
<223> OTHER INFORMATION: LCDR3 amino acid sequence

<400> SEQUENCE: 10

Ser Thr Trp Asp Asp Ser Leu Asp Gly Val Val
1               5                   10

<210> SEQ ID NO 11
<211> LENGTH: 19
<212> TYPE: PRT
<213> ORGANISM: Unknown
<220> FEATURE:
<223> OTHER INFORMATION: Anti-OSMR Heavy Chain Signal Peptide Amino
      Acid Sequence

<400> SEQUENCE: 11

Met Asp Phe Gly Leu Ser Leu Val Phe Leu Val Leu Ile Leu Lys Gly
1               5                   10                  15

Val Gln Cys

<210> SEQ ID NO 12
<211> LENGTH: 26
<212> TYPE: PRT
<213> ORGANISM: Unknown
<220> FEATURE:
<223> OTHER INFORMATION: Anti-OSMR Light Chain Signal Peptide Amino
      Acid Sequence

<400> SEQUENCE: 12

Met Ala Thr Gly Ser Arg Thr Ser Leu Leu Leu Ala Phe Gly Leu Leu
1               5                   10                  15
```

Cys Leu Ser Trp Leu Gln Glu Gly Ser Ala
            20                  25

<210> SEQ ID NO 13
<211> LENGTH: 220
<212> TYPE: PRT
<213> ORGANISM: Unknown
<220> FEATURE:
<223> OTHER INFORMATION: Anti-OSMR Heavy Chain Amino Acid Sequence -
      IgG4 CH1, Hinge, and CH2 Domains

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys
    210                 215                 220

<210> SEQ ID NO 14
<211> LENGTH: 106
<212> TYPE: PRT
<213> ORGANISM: Unknown
<220> FEATURE:
<223> OTHER INFORMATION: Anti-OSMR Heavy Chain Amino Acid Sequence -
      IgG1 CH3 Domain

<400> SEQUENCE: 14

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 15
<211> LENGTH: 326
<212> TYPE: PRT
<213> ORGANISM: Unknown
<220> FEATURE:
<223> OTHER INFORMATION: Anti-OSMR Heavy Chain Amino Acid Sequence -
      Constant Domain

<400> SEQUENCE: 15

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
```

```
                305                 310                 315                 320

Leu Ser Leu Ser Pro Gly
                325

<210> SEQ ID NO 16
<211> LENGTH: 105
<212> TYPE: PRT
<213> ORGANISM: Unknown
<220> FEATURE:
<223> OTHER INFORMATION: Anti-OSMR Light Chain Amino Acid Sequence -
      IgG Lambda Constant Domain

<400> SEQUENCE: 16

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100             105
```